United States Patent
Xie

(10) Patent No.: US 11,744,825 B2
(45) Date of Patent: *Sep. 5, 2023

(54) METHODS OF TREATING HYPERSENSITIVE COUGH OR ITCHING USING ION CHANNEL INHIBITORY COMPOUNDS

(71) Applicant: AFASCI, Inc., Redwood City, CA (US)

(72) Inventor: Xinmin Xie, Burlingame, CA (US)

(73) Assignee: AFASCI, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/115,549

(22) Filed: Aug. 28, 2018

(65) Prior Publication Data
US 2020/0069665 A1 Mar. 5, 2020

(51) Int. Cl.
*A61K 31/438* (2006.01)
*A61P 11/14* (2006.01)
*A61P 17/04* (2006.01)

(52) U.S. Cl.
CPC ............ *A61K 31/438* (2013.01); *A61P 11/14* (2018.01); *A61P 17/04* (2018.01)

(58) Field of Classification Search
CPC .......... A61K 31/438; A61P 11/14; A61P 17/04
See application file for complete search history.

(56) References Cited

U.S. PATENT DOCUMENTS

2018/0235931 A1   8/2018   Basta et al.

FOREIGN PATENT DOCUMENTS

WO   WO-2017083867 A1 * 5/2017   .......... A61K 31/4453

OTHER PUBLICATIONS

Zbarcea et al (Year: 2011).*
Chung (Year: 2011).*
Niimi (Year: 2015).*
Kian Fan Chung; "Approach to chronic cough: the neuropathic basis for cough hypersensitivity syndrome"; J Thorac Dis 2014; 6(S7):S699-S707.
Gibson et al.; "Mechanisms of cough"; Curr Opin Allergy Clin Immunol; Feb. 2014;14(1):55-61 (Abstract).
Chung et al.; "Chronic cough as a neuropathic disorder"; Lancet Respir Med; Jul. 2013;1(5):414-22.
Chung and Widdicombe (Eds); "Pharmacology and Therapeutics of Cough"; Handbook of Experimental Pharmacology; vol. 187; Springer-Verlag Berlin Heidelberg (2009) (Excerpt).
Morice et al.; "Expert opinion on the cough hypersensitivity syndrome in respiratory medicine"; Eur Respir J 2014; 44: 1132-1148.
International Preliminary Report on Patentability for PCT Appln PCT/US19/48666, dated Mar. 2, 2021, 8 pages.
Morjaria et al.; "Novel Antitussive Strategies"; Drug Discovery Today; vol. 18, Nos. 7/8 (pp. 380-388); Apr. 2013.
Pelletier et al.; "Dihydropyridine Receptor Blockade in the Treatment of Asthma"; Recent Patents on Inflammation & Allergy Drug Discovery 2008, 2, 109-116.
Ryan et al.; "An update and systematic review on drug therapies for the treatment of refractory chronic cough"; Expert Opinion on Pharmacotherapy; 19:7, 687-711 (2018).
Shi et al.; "Efficacy and Safety of Gabapentin in the Treatment of Chronic Cough: A Systematic Review"; Tuberc Respir Dis 2018; 81:167-174.
Song et al., "Changing the paradigm for cough: does 'cough hypersensitivity' aid our understanding?"; Asia Pac Allergy 2014;4:3-13.
Wang et al.; "Hydrogen sulfide-induced itch requires activation of Cav3.2 T-type calcium channel in mice"; Scientific Reports; 2015; 5:16768.
European Supplemental Search Report and Written Opinion for EP Appln EP19854290, dated Apr. 8, 2022.

* cited by examiner

*Primary Examiner* — Jeffrey S Lundgren
*Assistant Examiner* — Ibrahim D Bori
(74) *Attorney, Agent, or Firm* — Wei Zhang; Intelink Law Group, P.C.

(57) ABSTRACT

The present invention is directed towards new chemical entities which primarily inhibit the human T-type calcium channels and differentially modulate other key ion channels to control cell excitability, and abnormal neuronal activity, particularly involved in hypersensitive cough or itching.

6 Claims, 3 Drawing Sheets

METHODS OF TREATING HYPERSENSITIVE COUGH OR ITCHING USING ION CHANNEL INHIBITORY COMPOUNDS

STATEMENT OF GOVERNMENT RIGHTS

This invention was made with Government support under Grant 1 R44 NS086343-01 awarded by the National Institute of Neurological Disorders and Stroke, National Institute of Health. The Government has certain rights in this invention.

CROSS-REFERENCE TO RELATED APPLICATIONS

This application is related to PCT/US2016/061918, herein incorporated by reference in its entirety.

FIELD OF THE INVENTION

The field of the present invention relates to novel ion channel modulator compounds (inhibitors or antagonists of one type ion channel and/or combination of inhibition of multiple ion channels), compositions including ion channel modulators, and methods of treating conditions and disorders using the compounds and compositions. A more particular field involves compounds having selective T-type $Ca_{v3}$ channel inhibitory effects for mitigating hypersensitive/chronic cough or itching, pharmaceutical formulations including such compounds, and methods for selective treatment of hypersensitive cough or itching.

BACKGROUND OF THE INVENTION

Voltage-gated calcium ($Ca^{2+}$) channels (VGCC) play an integral role in the regulation of membrane ion conductance, cellular excitability and neurotransmitter release. VGCC are composed of the pore-forming α1 subunit and auxiliary α2δ ppm and β subunits that modulate channel expression and function. Among the low voltage activated channels is the $Ca_{v3}$ channel subtype, which mediates T-type calcium currents that may be targeted for treatment of epilepsy, especially children absence epilepsy and chronic pain (Huguenard, 1998, Cribbs et al., 2000, Perez-Reyes et al., 2009, Perez-Reyes, 2010).

The T-type or "low voltage-activated" calcium channels are so named because they open for shorter duration (T=transient) than the L-type (L=long lasting) calcium channels. T-type channels are activated at relatively negative membrane potentials (~−60 mV). In many types of neurons, $Ca^{2+}$ influx through T channels triggers low-threshold $Ca^{2+}$ spikes, which in turn elicit a burst of action potentials mediated by voltage-gated sodium ($Na^+$) channels. Brief burst firing is thought to play an important role in the synchronized activity of the thalamus and neuronal pacemaker under physiological conditions, but it also underlies a wide range of thalamocortical dysrhythmias under pathological conditions such as neuropathic pain or seizures. T channels can be activated by mild depolarization of the cell membrane (Talley et al., 1999, Perez-Reyes, 2003, Perez-Reyes, 2010, Pexton et al., 2011, Todorovic and Jevtovic-Todorovic, 2011).

Molecular cloning has revealed three distinct T channel proteins, designated $Ca_{v3.1}$, $Ca_{v3.2}$ and $Ca_{v3.3}$. The $Ca_{v3.1}$ and $Ca_{v3.3}$ channels are expressed predominantly, though not exclusively, in the CNS. In contrast, the $Ca_{v3.2}$ channel is not only present in the CNS, but also expressed in peripheral nerve cell bodies and nerve endings of afferent fibers (Huguenard, 1998, Cribbs et al., 2000, Perez-Reyes et al., 2009, Perez-Reyes, 2010). The $Ca_{v3.2}$ channel is highly expressed in dorsal root ganglion (DRG) neurons, whereas little $Ca_{v3.1}$ and virtually no $Ca_{v3.3}$ are expressed in the small diameter DRG neurons (Nelson et al., 1992). The $Ca_{v3.2}$ channels are also expressed at a lower level in several non-neuronal tissues, including heart, liver, kidney, and pituitary. Both diabetic neuropathy and chronic constriction injury models in rats lead to DRG neuron-specific upregulation of the $Ca_{v3.2}$ channel and the T current density. This pathological adaptation results in enhanced excitability of sensory neurons and causes hyperalgesia and allodynia (Jagodic et al., 2007, Jagodic et al., 2008, Latham et al., 2009, Messinger et al., 2009, Yue et al., 2013). Conversely, knockout or antisense knockdown of the $Ca_{v3.2}$ isoform produces analgesic effects (Messinger et al., 2009).

T-type channel inhibitors have two known uses in the clinic. The anti-absence seizure effects of ethosuximide and lamotrigine are thought to be mediated by the inhibition of T channel activity in the thalamus (Gomora et al., 2001, Huguenard, 2002). However, both drugs are weak and not specific against the T channel (Xie et al., 1995, Zhang et al., 1996). The antihypertensive effect of mibefradil is conventionally attributed to its inhibition of the T channel. However, mibefradil has poor selectivity with about 3-10 times more potent inhibition of the T-type than of the L-type $Ca^{2+}$ current or the voltage-gated $Na^+$ current (Avdonin et al., 2000). Because there are no selective T channel blockers, it is unclear whether and to what extend the inhibition of T channel activity at therapeutically relevant concentrations contributes to the therapeutic usefulness of a wide range of drugs.

Targeting a T-channel, particularly the $Ca_{v3.2}$ isoform, would be highly useful, for example, in reduction of thermal hyperalgesia and mechanical allodynia under pathological conditions such as diabetic neuropathy. Several efforts to discover potent and selective T-type $Ca^{2+}$ channels have been described in the literature, as exemplified below.

1,4-Substituted piperidines, for example, "compound 30" (3, 5-dichloro-N-{[1-(3,3-dimethylbutyl)-3-fluoropiperidin-4-yl]methyl}benzamide) and "TTA-P2" (3,5-dichloro-N-((1-((2,2-dimethyltetrahydro-2H-pyran-4-yl)methyl)-4-fluoropiperidin-4-yl)methyl)benzamide) were synthesized by Merck and found to potently block the T-Type Cav3.2 channel (J. Med. Chem. 51, 3692, (2008); J. Med. Chem. 51, 6471, (2008); US 2010/0222387; US 2013/8501773). TTA-A2 suppresses active wake, promotes slow-wave sleep (Kraus et al., 2010), and prevents weight gain in mice on a high-fat diet (Uebele et al., 2009).

A scaffold hopping approach afforded ML218 (3,5-Dichloro-N-[[(1α,5α,6-exo,6α)-3-(3,3-dimethylbutyl)-3-azabicyclo[3.1.0]hex-6-yl]methyl]benzamide, CID 45115620) a selective T-Type $Ca^{2+}$ inhibitor. ML218 possess acceptable in vivo rat PK and was efficacious in a preclinical Parkinson model. Thus, ML218 is a useful new biologic probe to study T-Type $Ca^{2+}$ function in vitro and in vivo (Xie et al., 2010, Xiang et al., 2011).

Certain lactam acetamides have been described by Abbott and others as $Ca_{v2.2}$ and $Ca_{v3.2}$ calcium channel blockers, and ABT-639 has been reported as a $Ca_{v3.2}$ calcium channel blocker for treatment of diabetic neuropathic pain through peripheral action, because ABT-639 is presumed to not penetrate the blood brain barrier (Jarvis et al., 2014).

N-Piperidinyl acetamide derivatives as calcium channel blockers have been described by Zalicus Pharmaceuticals, Ltd. (U.S. Pat. No. 8,569,344 (2013); U.S. Pat. No. 8,377, 968 (2013)). A piperidine-based compound, Z944, inhibits $Ca_{v3}$ channels in a voltage-dependent manner and is able to attenuate thalamic burst firing and suppress absence seizures in rats (Tringham et al., 2012). Z944 has shown promising results in clinical Phase I studies of pain in humans (Lee, 2014). Z944 is equivalent to AFA-258, described herein.

Despite the fact that many T-type $Ca^{2+}$ channel inhibitors have been discovered and have advanced to different stages of development, no FDA-approved selective T-type channel inhibitory compounds are available for clinical applications.

Cough is a physiological defense mechanism for the clearance of foreign materials and of excessive bronchial secretion in the airways, but it is also a common symptom of a variety of respiratory diseases. The cough reflex is triggered by the activation of rapidly adapting receptors (or irritant receptors) within the larynx, trachea and the proximal bronchi, and of C-fiber endings found in the airway walls of bronchi. Afferent signals are transmitted through the sensory vagal fibers to the cough center, which has been experimentally identified as being in the region of the solitary nucleus in the medulla within the brain (Kase Wakita et al. 1970). From the cough center, the impulses travel through the efferent pathways to the respiratory muscles (diaphragm, intercostal and abdominal muscles) and the airways (Irwin, Rosen et al. 1977).

Experimental studies have shown that peripheral neurons may be involved in "hypersensitive cough." This type of cough is a chronic/persistant cough that can result from an acute cough, or from a cough syndrome or disease such as COPD, asthma, GI reflux, post-nasal drip syndrome and exposure to pollutants including smog and sildfire smoke (see, e.g., Chung and Widdicombe, The Pharmacology and Therapeutics of Cough, In Handbook of Experimental Pharmacology ISSN 0171-2004, Library of Congress Control Number: 200892959, 2009 Springer-Verlag Berlin Heidelberg).

Similar to cough, which is a defensive mechanism to eliminate irratants or pathogens within the airway under physiological conditions, itch is also a defensive mechanism to protect our body against bugs, harmful chemicals and poisonous plants by causing scratching responses. However, persistant or chronic itchy skin (pruritus) under pathological conditions is a significant unmet clinical problem. Over 30 million people in U.S. suffer from eczema, including atopic dermatitis, and about 7 million people suffer from psoriasis. Furthermore, pruritus can be a symptom of an underlying internal disease, including liver disease, kidney failure, iron deficiency anemia, thyroid problems or cancers, such as leukemia and lymphoma. In hemodialysis patients, the prevalence of chronic kidney disease associated pruritus is high as 55% in both men and women (Prevalence of chronic kidney disease-associated pruritus among adult dialysis patients: A meta-analysis of cross-sectional studies, Hu et al.).

Currently, there is no efficient therapy for the irresistible itch symptoms of various chronic diseases associated pruritus or itching. A recent study implicated Cav 3.2 channel activation in NaHS-induced itching in experimental animals (Wang et al., Scientific Reports 5:16768 (2015), suggesting the Cav 3.2 channel might be a target for anti-iching compounds.

In fact, the present inventors have discovered that T-type $Ca^{2+}$ channel inhibitors disclosed herein are useful for the treatment and prevention of hypersensitive cough; for example, EX-17, EX-128, EX-130 and EX-132. The present inventors have also discovered that T-type $Ca^{2+}$ channel inhibitors disclosed herein are useful for the treatment and prevention of itching, for example, EX-31, EX-55, EX-130, EX-132 and AFA-258 (i.e., Z944 from Zalicus Pharmaceuticals), AFA-309 and AFA-358. The highly potent and selective T-type $Ca^{2+}$ channel inhibitors, EX-128 and AFA-258 did not produce anti-itching effects in both of the itch models, chloroquine- and histamine-induced itching. Unexpectedly, however, compounds that are mixed modulators of key ion channels, including voltage-gated Na channels, exemplified by EX-31, EX-130 and AFA-358, are effective against both chloroquine- and histamine-induced models of itching.

SUMMARY OF THE INVENTION

The current invention provides compounds, formulations and methods of use for the treatment and prevention of hypersensitive cough and/or itching, in which key ion channels, particularly the T-type $Ca^{2+}$ channels are involved. The compounds and methods can be used in both human and veterinary medicine.

In one aspect, the invention provides a method of treating chronic cough, the method comprising the step of administering a therapeutically effective amount of a compound, or a pharmaceutically acceptable salt thereof, wherein the compound is:

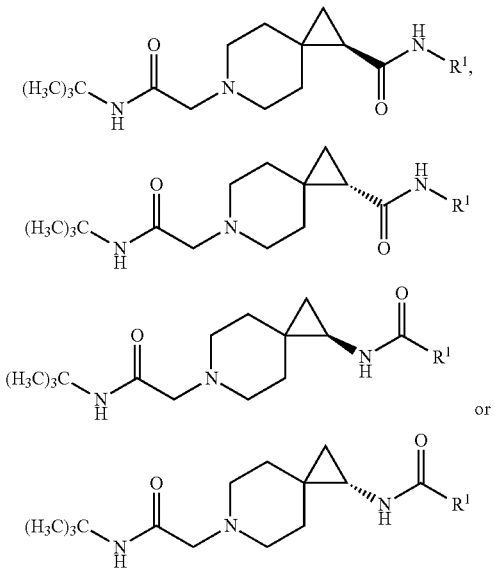

wherein $R^1$ is phenyl substituted with one to three substituents, each of which is a member selected from the group consisting of F, Cl, and $CF_3$, thereby treating chronic cough.

In one embodiment, the compound is:

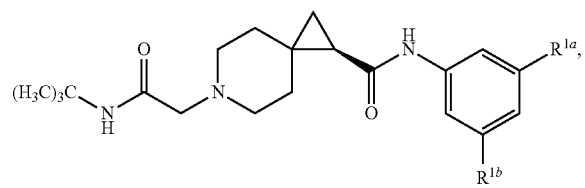

-continued

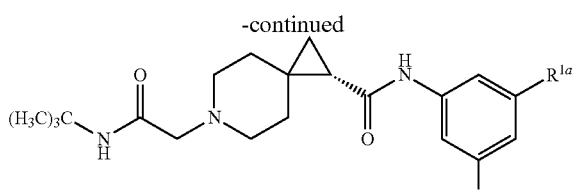

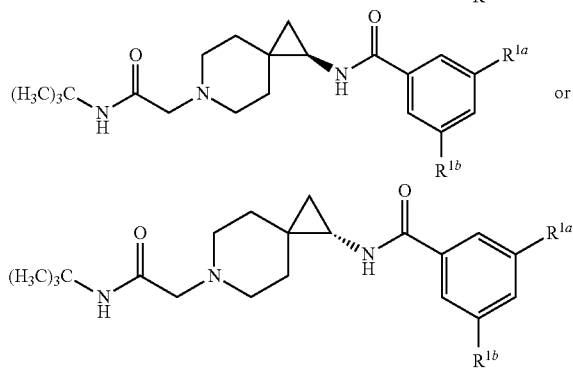

wherein R$^{1a}$ and R$^{1b}$ are members each independently selected from the group consisting of F, Cl, and CF$_3$.

In another embodiment, the compound is:

EX-17

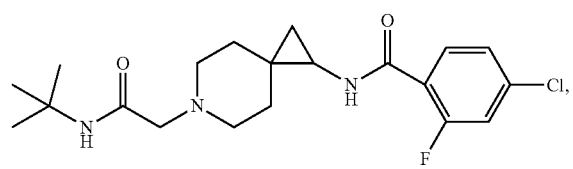

EX-128

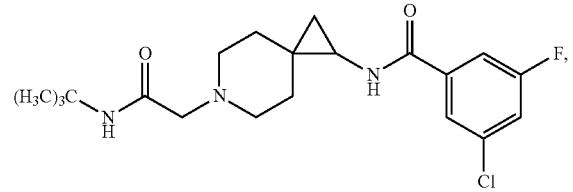

EX-130

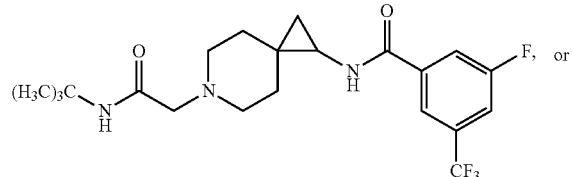

EX-132

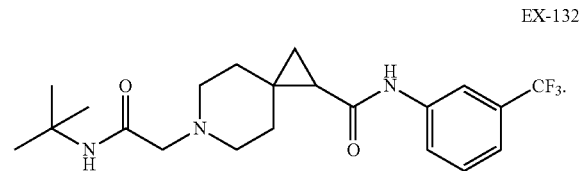

In another embodiment, the hypersensitive or chronic cough is caused by a disease or syndrome selected from the group consisting of COPD, asthma, GI reflux, post-nasal drip syndrome and chronic exposure to pollutants.

In another embodiment the compound is administered orally or nasally.

In one aspect, the method comprising the step of administering a therapeutically effective amount of a compound, or a pharmaceutically acceptable salt thereof, wherein the compound is selected from the group consisting of:

EX-31

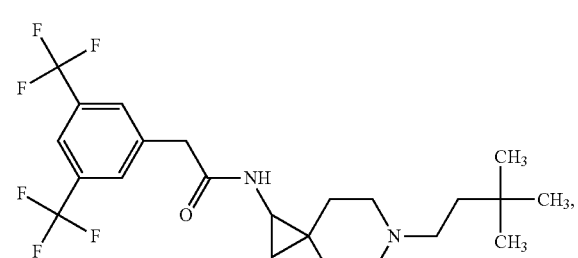

EX-55

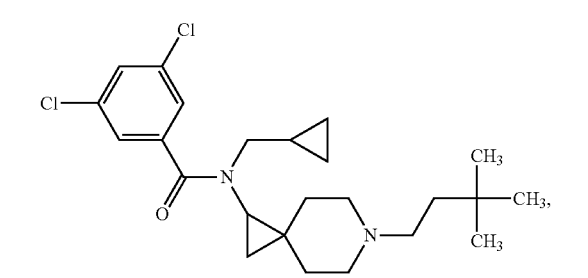

EX-130

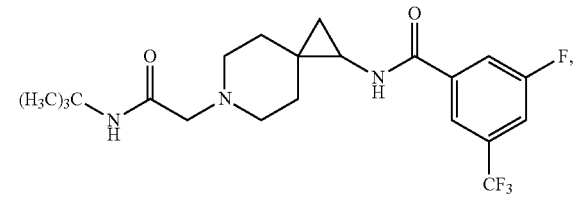

EX-132

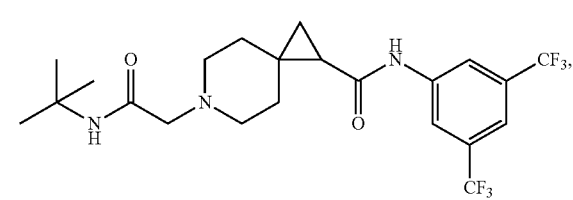

AFA-258 (Z944)

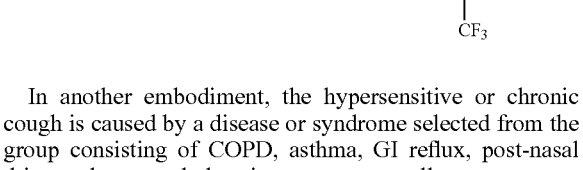

AFA-309

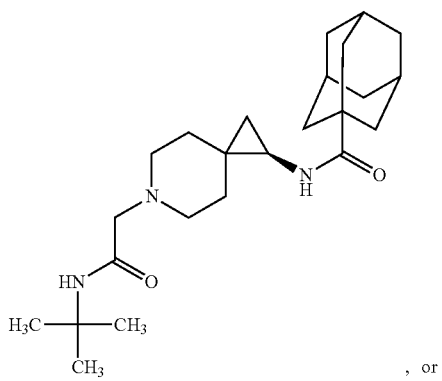

, or

AFA-358

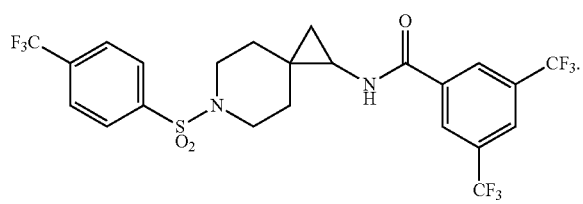

In one embodiment, the itching is caused by atopic dermatitis, psoriasis, kidney failure, cholestasis, diabetes, leukemia, lymphoma, eczema, liver failure, anemia, thyroid disease, toxic plant exposure, chemical exposure, smog exposure, insect bites or allergic reaction to a food allergan.

In another embodiment, the compound is administered orally or nasally.

In another aspect, the invention provides method of treating itching, the method comprising the step of administering a therapeutically effective amount of a compound, or a pharmaceutically acceptable salt thereof, wherein the compound is selected from the group consisting of:

EX-31

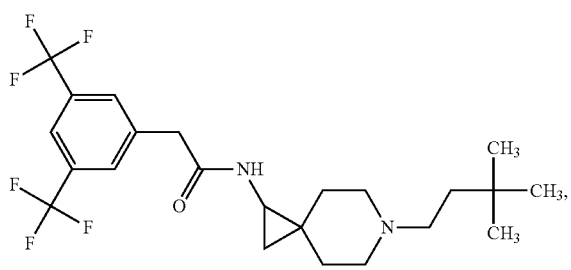

EX-130

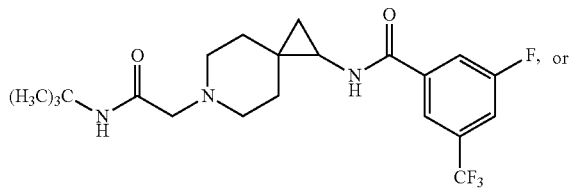

AFA-358

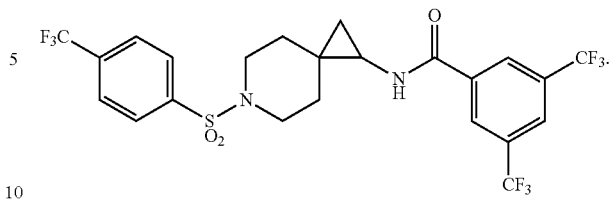

In one embodiment, the itching is caused by atopic dermatitis, psoriasis, kidney failure, cholestasis, diabetes, leukemia, lymphoma, eczema, liver failure, anemia, thyroid disease, toxic plant exposure, chemical exposure, smog exposure, insect bites or allergic reaction to a food allergan.

In another embodiment, the compound is administered orally or nasally.

BRIEF DESCRIPTION OF THE DRAWINGS

FIG. 1A. Effects of a representative compound EX-17 at three doses (3, 10 and 30 mg/kg) and the benchmark dextromethorphan (60 mg/kg) on the number of cough events were determined in a model of citric acid-induced cough in naïve, conscious guinea pigs. All test compounds were formulated with 0.5% hydroxyl Propyl Cellulose and given orally by gavage (p.o.). Data are given as mean±SEM of n=8 animals per group. P-value (<0.05 indicated by *) represent significant difference compared with the vehicle-treated control group using one-way ANOVA followed by Fisher's LSD post-hoc test.

DETAILED DESCRIPTION OF THE INVENTION

Figure 1A:
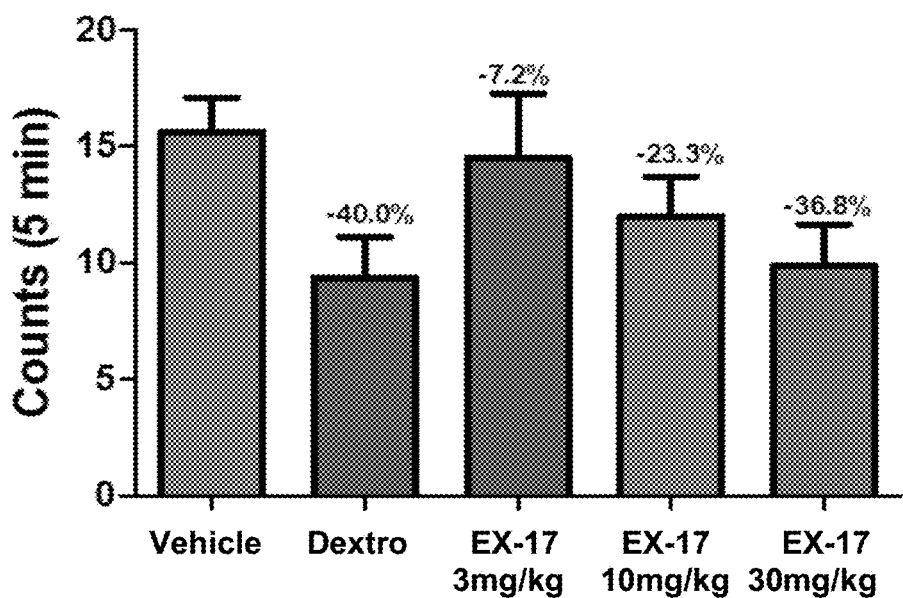
FIG. 1A.

As described herein, the present invention provides new methods of treating hypersensitive or chronic cough using inhibitors of selective T-type channel inhibitory compounds.

Chronic cough a symptom caused by a variety of respiratory disorders affects the quality of life and further exacerbates respiratory pathological conditions. Pharmacological interventions are currently confined to treating the cause of cough, and symptomatic treatment options controlling the cough per se with an acceptable therapeutic index are also limited. The centrally acting cough therapy, such as dextromethorphan and codeine, both of which are opiates used as a cough suppressant in the clinic, depresses the cough center, and is considered the most clinically effective, although sedative and addictive effects can limit their use. Local anesthetics that interfere with the conduction of afferent nerve impulses have been shown to be peripherally active antitussive compounds, but their considerable side effects make their use unsuitable. Extracellular adenosine 5'-triphosphate (ATP) activates P2X receptors in cell surface and in primary afferent nerves. The development of selective blockers of different P2X receptors has led to clinical trials of their effectiveness in the management of cough, pain, inflammation and certain neurodegenerative diseases (North 2016).

In contrast, little is known about the role of T-type $Ca^{2+}$ channels in cough reflex and in persistent cough under pathological conditions. Although T-type $Ca^{2+}$ channels, mainly the Cav3.2 subtype expressed in nodose ganglion (Pachuau and Martin-Caraballo, 2007) and play a role in modulation of its axons, vagal nerve excitability, the conventional T-type $Ca^{2+}$ channel locker $Ni^{2+}$ (300 µM) apparently did not alter the responses of guinea pig tracheobronchial cough receptor fibers or nociceptors to citric acid (Canning and Chou, 2004). Therefore, the possible efficacy of T-type $Ca^{2+}$ channel modulators with regard to antitussive property in a model of citric acid-induced cough in guinea pigs was investigated using new compounds (for example, EX-17, EX-128, EX-130 and EX-132) that potently and selectively inhibit the T-type $Ca^{2+}$ channels (see, e.g., PCT/US2016/061918, herein incorporated by reference in its entirety) and compared the results to a clinically used treatment with dextromethorphan.

Many chronic itch disorders are not responsive to commonly used anti-histamine drugs suggesting that histamine-independent itch models may be more relevant for identification of novel target and discovery of new compounds for chronic itch treatment. A recent identification of the first spinal cord itch receptor, gastrin-releasing peptide receptor (GRPR) triggered extensive molecular studies of itch transmission pathways in the nervous system. GRP-GRPR signaling mediates histamine-independent pathway both in acute and chronic itch. Which ion channels mediated the specific itching signaling pathway are currently unknown, though a variety of ion channels such as the voltage-gated sodium (Na) channel, N-type Cav2.2, the T-type Cav3.2 channels and transient receptor potential vanilloid 1 (TRPV1) channels have been suggested to be involved in itch transmission pathways (J Neurol Sci. 1999 Jan. 15; 162(2):162-8. Positive symptoms in multiple sclerosis: their treatment with sodium channel blockers, lidocaine and mexiletine. Sakurai M I, Kanazawa I.). Therefore, the possible efficacy of T-type $Ca^{2+}$ channel modulators with regard to anti-itching properties in two different model of itch in mice was investigated using new compounds (for example, EX-31, EX-55, EX-130, EX-132, AFA-258, AFA-309 and AFA-358) that potently and selectively inhibit the T-type $Ca^{2+}$ channels (see, e.g., PCT/US2016/061918, herein incorporated by reference in its entirety)

Below are definitions of representative types of hypersensitive cough and itching in which the compounds, pharmaceutical formulations and methods find use in treating.

The term "method of treating hypersensitive or chronic cough" means partial or full relief from the symptoms of cough or the prevention of hypersensitive cough, often defined as chronic couch of more than eight weeks in duration, including the descriptions of hypersensitive cough provided herein. The hypersensitive or chronic cough can be caused by a disease or syndrome selected from the group consisting of COPD, asthma, GI reflux, post-nasal drip syndrome and chronic exposure to pollutants such as smog and wildfire smoke.

The term "method of treating itching" means partial or full relief from the symptoms of itching or the prevention of itching. The itching can be caused by atopic dermatitis, psoriasis, kidney failure, cholestasis, diabetes, leukemia, lymphoma, eczema, liver failure, anemia, thyroid disease, toxic plant exposure, chemical exposure, smog exposure, insect bites or allergic reaction to a food allergan.

"Compound of the invention," as used herein, refers to the compounds discussed herein and salts (e.g. pharmaceutically acceptable salts) of these compounds.

"Alkyl" is intended to embrace a univalent saturated linear or branched hydrocarbon chain having the number of carbon atoms specified, or if no number is specified, having 1 to 8 carbon atoms. "Alkylene" refers to a similar group, which is divalent. "Optionally substituted" alkyl refers to either an unsubstituted alkyl group, or an alkyl group substituted with one or more substituents (such as one, two, three, four, or five substituents) selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH ($C_1$-$C_4$ alkyl), —N($C_1$-$C_4$ alkyl)($C_1$-$C_4$ alkyl) (where each $C_1$-$C_4$ alkyl is chosen independently of the other), —$NO_2$, —CN, isocyano (NC—), oxo (=O), —C(=O)H, —C(=O)—($C_1$-$C_4$ alkyl), —COOH, —C(=O)—O—($C_1$-$C_4$ alkyl), —C(=O)$NH_2$, —C(=O)NH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH, —S—($C_1$-$C_4$ alkyl), —S(=O)—($C_1$-$C_4$ alkyl), —$SO_2$—($C_1$-$C_4$ alkyl), and —$SO_2$—($C_1$-$C_4$ perfluoroalkyl). Examples of such substituents are —$CH_3$, —$CH_2CH_3$, —$CF_3$, —$CH_2CF_3$, —$CF_2CF_3$, —$OCH_3$, —NH($CH_3$), —N($CH_3$)$_2$, —$SCH_3$, and $SO_2CH_3$. "Optionally substituted alkylene" groups can be unsubstituted, or substituted in the same manner as substituted alkyl groups.

"Cycloalkyl" is intended to embrace a univalent saturated cyclic hydrocarbon chain having the number of carbon atoms specified, or if no number is specified, having 3 to 10 carbon atoms, or 3 to 8 carbon atoms, preferably 3 to 6 carbon atoms. "Cycloalkylene" refers to a similar group, which is divalent. Cycloalkyl and cycloalkylene groups can be unsubstituted, or substituted in the same manner as substituted alkyl groups.

"Alkenyl" is intended to embrace a univalent linear or branched hydrocarbon chain having at least one carbon-carbon double bond, and having the number of carbon atoms specified, or if no number is specified, having 2 to 8 carbon atoms. "Alkenylene" refers to a similar group, which is divalent. Alkenyl and alkenylene groups can be unsubstituted, or substituted in the same manner as substituted alkyl groups where chemically possible.

"Cycloalkenyl" is intended to embrace a univalent cyclic hydrocarbon chain having at least one carbon-carbon double bond and having the number of carbon atoms specified, or if no number is specified, having 4 to 10 carbon atoms, or 4 to 8 carbon atoms, or 4 to 6 carbon atoms. "Cycloalkenylene" refers to a similar group, which is divalent. Cycloalkenyl and cycloalkenylene groups can be unsubstituted, or substituted in the same manner as substituted alkyl groups where chemically possible.

"Alkynyl" is intended to embrace a univalent linear or branched hydrocarbon chain having at least one carbon-carbon triple bond, and having the number of carbon atoms specified, or if no number is specified, having 2 to 8 carbon atoms. "Alkynylene" refers to a similar group, which is divalent. Alkynyl and alkynylene groups can be unsubstituted, or substituted in the same manner as substituted alkyl groups where chemically possible.

"Aryl" is defined as a univalent aromatic ring system. Aryl groups include monocyclic aromatic rings and polycyclic aromatic ring systems containing the number of carbon atoms specified, or if no number is specified, containing six to twenty carbon atoms. In other embodiments, aryl groups may contain six to ten carbon atoms. Non-limiting examples of aryl and heteroaryl groups include phenyl, 1-naphthyl, 2-naphthyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In some embodiments, aryl groups can be unsubstituted. In other embodiments, aryl groups can be substituted with, for example, one, two, three or more substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —$NO_2$, —CN, (NC—), —C(=O)H, —C(=O)—($C_1$-$C_4$ alkyl), —COOH, —C(=O)—O—($C_1$-$C_4$ alkyl), —C(=O)$NH_2$, —C(=O)NH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. In some embodiments, any of the aryl and heteroaryl groups is optionally substituted, e.g., with one or more groups referred to herein as an "aryl group substituent". "Arylene" refers to a similar group, which is divalent.

The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom.

"Hydrocarbyl" is defined as a univalent hydrocarbon group, that is, a group comprised of hydrogen and carbon, whether aliphatic or aromatic, acyclic or cyclic, or any combination of, or all of, aliphatic, aromatic, acyclic and cyclic. Hydrocarbyl groups have the number of carbon atoms specified, or if no number is specified, having 1 to 10 carbon atoms. "Hydrocarbylene" refers to a similar group, which is divalent. Hydrocarbyl and hydrocarbylene groups can be unsubstituted, or substituted in the same manner as substituted alkyl groups where chemically possible.

"Heterocycle" or a "heterocyclic group" is defined as a ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus. "Heteroaryl" is defined as an aromatic ring system which contains the number of carbon atoms specified, and one or more heteroatoms (such as one to six heteroatoms, or one to three heteroatoms, or one heteroatom), where heteroatoms include, but are not limited to, oxygen, nitrogen, sulfur, and phosphorus; heteroaryl groups are a subset of heterocyclic groups. In some embodiments, heteroatoms for heterocyclyl and heteroaryl groups are selected from the group consisting of oxygen and nitrogen. In various embodiments, heterocyclic groups may contain two to twenty carbon atoms and one to six heteroatoms, two to twelve carbon atoms and one to four heteroatoms, two to twelve carbon atoms and one to three heteroatoms, two to ten carbon atoms and one to three heteroatoms, two to six carbon atoms and one to three heteroatoms, or two to six carbon atoms and two to four heteroatoms. In some embodiments, heterocyclic groups can be unsubstituted. In other embodiments, heterocyclic groups can be substituted on any chemically possible valence with for example, one, two, or three substituents independently selected from the group consisting of —OH, —($C_1$-$C_4$ alkyl)-OH, halo, fluoro, chloro, bromo, iodo, —($C_1$-$C_4$ alkyl), —($C_1$-$C_4$) haloalkyl, —($C_1$-$C_4$) perhaloalkyl, —O—($C_1$-$C_4$ alkyl), —O—($C_1$-$C_4$ haloalkyl), —O—($C_1$-$C_4$ perhaloalkyl), —($C_1$-$C_4$) perfluoroalkyl, —(C=O)—($C_1$-$C_4$) alkyl, —(C=O)—($C_1$-$C_4$) haloalkyl, —(C=O)—($C_1$-$C_4$) perhaloalkyl, —$NH_2$, —NH($C_1$-$C_4$ alkyl), —N($C_1$-$C_4$ alkyl)($C_1$-$C_4$ alkyl) (where each $C_1$-$C_4$ alkyl is chosen independently of the other), —$NO_2$, —CN, (NC—), —C(=O)H, —C(=O)—($C_1$-$C_4$ alkyl), —COOH, —C(=O)—O—($C_1$-$C_4$ alkyl), —C(=O)$NH_2$, —C(=O)ONH($C_1$-$C_4$ alkyl), —C(=O)N($C_1$-$C_4$ alkyl)($C_1$-$C_4$ alkyl) (where each $C_1$-$C_4$ alkyl is chosen independently of the other), —SH, —($C_1$-$C_4$ alkyl)-SH and —S—$C_1$-$C_4$ alkyl. Examples of heterocycles include aziridine, oxirane, oxetane, azetidine, pyrrolidine, pyrrole, tetrahydrofuran, furan, thiolane, thiophene, imidazolidine, imidazole, pyrazolidine, pyrazole, 1,2,3-triazole, 1,2,4-triazole, piperidine, pyridine, pyran, piperazine, and morpholine.

A "heteroalkyl" group is defined as a univalent hydrocarbyl group, where one or more of the carbon atoms have been independently replaced by a heteroatom at any chemically possible location, where heteroatoms include, but are not limited to, oxygen, nitrogen, sulfur, and phosphorus. Heteroalkyl groups have the number of carbon atoms specified, or if no number is specified, having 1 to 10 carbon atoms, and also at least one heteroatom, such as 1 to 5 heteroatoms, 1 to 4 heteroatoms, 1 to 3 heteroatoms, 1 to 2 heteroatoms, or one heteroatom. "Heteroalkylene" refers to a similar group, which is divalent. Heteroalkyl and heteroalkylene groups can be unsubstituted, or substituted in the same manner as substituted alkyl groups where chemically possible. Examples of heteroalkyl and heteroalkylene groups include, but are not limited to, ethylene glycol and polyethylene glycol moieties, such as (—$CH_2CH_2$—O—)$_n$—H (a monovalent heterohalkyl group) and (—$CH_2CH_2$—O—)$_n$ (a divalent heteroalkylene group) where n is an integer from 1 to 12 inclusive, and propylene glycol and polypropylene glycol moieties, such as (—$CH_2CH(CH_3)$—O—)$_n$—H (a monovalent heteroalkyl group) and (—$CH_2CH(CH_3)$—O—)$_n$— (a divalent heteroalkylene group) where n is an integer from 1 to 12 inclusive. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The various groups described above can be attached to the remainder of the molecule at any chemically possible location on the fragment, including attachment via a substituent when the group is substituted. For the purposes of drawing the structures, groups are typically attached by replacement of a hydrogen, hydroxyl, methyl, or methoxy group on a "complete" molecule to generate the appropriate fragment, and a bond is drawn from the open valence on the fragment to the remainder of the molecule. For example, attachment of the heteroalkyl group —$CH_2$—O—$CH_3$ proceeds by removal of a hydrogen from one of the methyl groups of $CH_3$—O—$CH_3$, to generate the heteroalkyl fragment —$CH_2$—O—$CH_3$, from which a bond is drawn from the open valence to the remainder of the molecule.

Reference to "about" a value or parameter herein includes (and describes) variations that are directed to that value or parameter per se. For example, description referring to "about X" includes description of "X".

The terms "a" or "an," as used in herein means one or more, unless the context clearly indicates otherwise.

By "subject," "individual," or "patient" is meant an individual organism, preferably a vertebrate, more preferably a mammal, most preferably a human.

The description is intended to embrace all salts of the compounds described herein, as well as methods of using such salts of the compounds. In one embodiment, the salts of the compounds comprise pharmaceutically acceptable salts. Pharmaceutically acceptable salts are those salts which can be administered as drugs or pharmaceuticals to humans and/or animals and which, upon administration, retain at least some of the biological activity of the free compound (neutral compound or non-salt compound). The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such as lysine salts, can also be prepared. For lists of pharmaceutically acceptable salts, see, for example, P. H. Stahl and C. G. Wermuth (eds.) "Handbook of Pharmaceutical Salts, Properties, Selection and Use" Wiley-VCH, 2011 (ISBN: 978-3-90639-051-2). Several pharmaceutically acceptable salts are also disclosed in Berge, J. Pharm. Sci. 66:1 (1977).

The phrase "therapeutically effective amount" as used herein means that amount of a compound, material, or formulation comprising a compound of the present invention which is effective for producing some desired therapeutic effect by inhibition of a T-Channel in at least a subpopulation of cells in an animal, thereby blocking or lessening the biological consequences of that pathway in the treated cells, at a reasonable benefit/risk ratio applicable to any medical treatment.

In an exemplary embodiment, the invention provides a method for treating a condition described herein in a mammal, the method comprises administering to the mammal a therapeutically effective amount of a compound described herein, or a compound according to a formula described herein, or a pharmaceutically acceptable salt thereof, sufficient to treat the condition, thereby treating the condition. In an exemplary embodiment, according to any method described herein, the mammal is in need of treatment with the compound. In an exemplary embodiment, according to any method described herein, the mammal is a dog, a cat, a horse, a pig, a cow, a sheep, a mouse, a guinea pig, or a rat. In an exemplary embodiment, according to any method described herein, the mammal is a human.

In an exemplary embodiment, the invention provides a method for treating a condition described herein in a mammal, the method comprises administering to the mammal a therapeutically effective amount of a pharmaceutical formulation described herein, sufficient to treat the condition, thereby treating the condition. In an exemplary embodiment, according to any method described herein, the mammal is in need of treatment with the pharmaceutical formulation. In an exemplary embodiment, according to any method described herein, the mammal is not otherwise in need of treatment with the pharmaceutical formulation. In an exemplary embodiment, according to any method described herein, the mammal is a mouse or a rat. In an exemplary embodiment, according to any method described herein, the mammal is a human.

The term "$IC_{50}$" refers to the concentration causing a 50% inhibition of the specific binding of the control substance.

The following abbreviations may be used herein:
~ about
+ve or pos. ion positive ion
Δ heat
Ac Acetyl can acetonitrile
Ac₂O acetic anhydride
Aq aqueous
AcOH acetic acid
Bn benzyl
Boc tert-butyloxycarbonyl
BOP-Cl Bis(2-oxo-3-oxazolidinyl)phosphinic chloride
BSA bovine serum albumin
Bu butyl
Bz benzoyl
Calcd or Calc'd calculated
Cbz carboxybenzyloxy, benzylcarbamate
Conc. concentrated
δ NMR, chemical shift in parts per million (ppm)
D day(s) or doublet (NMR)
DBU 1,8-diazabicyclo[5.4.0]undec-7-ene
DCE dichloroethane
DCM dichloromethane
DDQ 2,3-dichloro-5,6-dicyano-1,4-benzoquinone
DEA diethylamine
DIEA or DIPEA diisopropylethylamine
DMAP 4-dimethylaminopyridine
DME 1,2-dimethoxyethane
DMF N,N-dimethylformamide
DMP Dess-Martin periodinane; 1,1,1-triacetoxy-1,1-dihydro-1,2-benziodoxol-3(1H)-one
DMSO dimethyl sulfoxide
DPPA Diphenylphosphoryl azide
DRG Dorsal Root Ganglion
EDC or EDCI N-ethyl-N'-(3-dimethylaminopropyl)carbodiimide
EGTA ethylene glycol tetraacetic acid
Eq equivalent
ESI or ES electrospray ionization
Et ethyl
Et₂O diethyl ether
Et₃N triethylamine
EtOAc ethyl acetate
EtOH ethyl alcohol
G gram(s)
H hour(s)
O-(7-azabenzotriazol-1-yl)-N,N,N',N'-tetramethyluronium hexafluorophosphate
O-benzotriazole-N,N,N',N'-tetramethyl-uronium-hexafluorophosphate
HEPES 4-(2-hydroxyethyl)-1-piperazineethanesulfonic acid
Hex hexanes
HMPA hexamethylphosphoramide
HOAt 1-hydroxy-7-azabenzotriazole
HOBT hydroxybenzotriazole
HPLC high pressure liquid chromatography
IPA or iPrOH isopropyl alcohol
KOAc potassium acetate
LCMS, LC-MS or LC/MS liquid chromatography mass spectrometry
LDA lithium diisopropylamide
LHMDS or LiHMDS lithium hexamethyldisilazide
M molar (mol L⁻¹)
Me methyl
MeCN acetonitrile
MeI iodomethane
MeOH methyl alcohol
Mg milligram(s)
min minute(s)
mL milliliter(s)
M mole(s)
MS mass spectrometry
MsCl methanesulfonyl chloride
MTBE or MtBE methyl tert-butyl ether
m/z mass-to-charge ratio
NaHMDS sodium hexamethyldisilazide
NaOtBu sodium tert-butoxide
NBS N-bromosuccinimide
nBuLi n-butyl lithium
NMO N-methylmorpholine-N-oxide
NMP 1-methyl-2-pyrrolidinone
NMR nuclear magnetic resonance
PBS phosphate buffered saline
PMB paramethoxybenzyl
Pr propyl
Prep-HPLC Preparative high pressure liquid chromatography
Ppm parts per million
p-tol para-toluoyl
PTZ pentylenetetrazole
Rac racemic
RP-HPLC or RPHPLC reversed phase high pressure liquid chromatography
RT or rt or r.t. room temperature
sat or sat'd or satd Saturated
SNI Spared nerve injury
SNL Spinal nerve ligation
TBAF tetrabutylammonium fluoride
TBDMS tert-butyldimethylsilyl
TBDMS-Cl tert-butyldimethylsilyl chloride
TBDPS tert-butyldiphenylsilyl
TEMPO (2,2,6,6-tetramethylpiperidin-1-yl)oxidanyl
tert or t tertiary
TFA or TFAA triflouroacetic acid
THF tetrahydrofuran
TLC thin layer chromatography
TMS trimethylsilyl or trimethylsilane
$t_R$ retention time
tBuOH tert-butyl alcohol
v/v volume per volume In one aspect the invention provides a compound of the invention. In an exemplary embodiment, the invention provides a compound described herein, or a salt thereof. In an exemplary embodiment, the salt of a compound described herein is a pharmaceutically acceptable salt. In an exemplary embodiment, the invention provides a compound described herein, or a pharmaceutically acceptable salt thereof. In an exemplary embodiment, the invention provides a compound described in a formula provided herein. In an exemplary embodiment, the invention provides a compound described herein.

One object of the present invention is to provide a compound, or a pharmaceutically acceptable salt thereof, which can be used to treat chronic cough or itching, of the general structure:

(I)

wherein $R^1$ is substituted or unsubstituted alkyl, substituted or unsubstituted aryl or substituted or unsubstituted heteroaryl; X is selected from —N(R$^{14}$)—C(=O)—, or —N(R$^{14}$)—S(=O)$_k$—, or —CH$_2$—N(R$^{14}$)—C(=O)—, or —CH$_2$—N(R$^{14}$)—S(=O)$_k$—, or C(=O)—N(R$^{14}$), and —CH$_2$—C(=O)—N(R$^{14}$), or CH$_2$—N(R$^{14}$); k is selected from 1 and 2; and R$^{14}$ is H or substituted or unsubstituted C$_1$-C$_6$ alkyl or substituted or unsubstituted cycloalkyl, or substituted or unsubstituted heteroalkyl; R$^2$ is selected from substituted or unsubstituted alkyl and substituted or unsubstituted heteroalkyl; R$^3$, R$^4$, R$^5$, R$^6$ are each independently hydrogen, substituted or unsubstituted —C$_{1-6}$ alkyl, substituted or unsubstituted —C$_{1-6}$ haloalkyl, a 3-, 4-, 5- or 6-membered substituted or unsubstituted cycloalkyl or substituted or unsubstituted heterocycloalkyl group, wherein R$^3$ and R$^4$ along with the carbon to which they are attached optionally form a 3- to 6-membered substituted or unsubstituted cycloalkyl or substituted or unsubstituted heterocycloalkyl group, said heterocycloalkyl group optionally containing 1 or 2 heteroatoms independently selected from O, N or S, and said substituted cycloalkyl or substituted heterocycloalkyl group is optionally substituted with 1, 2, or 3 substituents independently selected from F, —C$_{1-6}$ alkyl, and —CF$_3$. R$^5$ and R$^6$, together with the carbon to which they are attached, optionally form a 3-, 4-, 5- or 6-membered substituted or unsubstituted cycloalkyl or substituted or unsubstituted heterocycloalkyl group, said heterocycloalkyl group optionally containing 1 or 2 heteroatoms independently selected from O, N or S, and said cycloalkyl or heterocycloalkyl group is optionally substituted with from 1, 2 or 3 substituents independently selected from F, —C$_{1-6}$ alkyl, and —CF$_3$. R$^7$, R$^8$, R$^9$, and R$^{10}$ are each independently hydrogen, fluorine, substituted or unsubstituted-C$_{1-6}$ alkyl, substituted or unsubstituted-C$_{1-6}$ haloalkyl, a 3-, 4-, 5- or 6-membered substituted or unsubstituted cycloalkyl or substituted or unsubstituted heterocycloalkyl group, wherein R$^7$ and R$^8$, together with the carbon to which they are attached, optionally form a 3-, 4-, 5-, or 6-membered substituted or unsubstituted cycloalkyl or substituted or unsubstituted heterocycloalkyl group, said heterocycloalkyl group optionally containing 1 or 2 heteroatoms independently selected from O, N or S, and said substituted cycloalkyl or substituted heterocycloalkyl group is optionally substituted with 1, 2 or 3 substituents independently selected from F, —C$_{1-6}$ alkyl, or —CF$_3$; R$^9$ and R$^{10}$, together with the carbon to which they are attached, optionally form a 3-, 4-, 5- or 6-membered substituted or unsubstituted cycloalkyl or substituted or unsubstituted heterocycloalkyl group, said heterocycloalkyl group containing from 1 or 2 heteroatoms independently selected from O, N or S, and the substituted cycloalkyl or substituted heterocycloalkyl group is optionally substituted with 1, 2, or 3 substituents independently selected from F, —C$_{1-6}$ alkyl, or —CF$_3$; R$^{11}$, R$^{12}$ and R$^{13}$ are each independently hydrogen, fluorine, substituted or unsubstituted-C$_{1-6}$ alkyl, substituted or unsubstituted-C$_{1-6}$ haloalkyl, a 3-, 4-, 5- or 6-membered substituted or unsubstituted cycloalkyl or substituted or unsubstituted heterocycloalkyl group, wherein R$^{11}$ and either R$^{12}$ or R$^{13}$, together with the carbons to which they are attached, optionally form a 3-, 4-, 5-, 6- or 7-membered substituted or unsubstituted cycloalkyl or substituted or unsubstituted heterocycloalkyl group.

In an exemplary embodiment, wherein R$^2$, R$^3$, R$^4$, R$^5$, R$^6$, R, R$^8$, R$^9$, R$^{10}$, R$^{11}$, R$^{12}$, R$^{13}$, and X are as described herein, R$^1$ is selected from substituted or unsubstituted benzyl or a substituted or unsubstituted polycyclic cycloalkyl ring, e.g., adamantyl. In an exemplary embodiment, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is substituted adamantyl. In an exemplary embodiment, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is substituted adamant-1-yl. In an exemplary embodiment, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is unsubstituted adamantyl. In an exemplary embodiment, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is unsubstituted adamant-1-yl.

In an exemplary embodiment, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is substituted by 1, 2, 3 or 4 non-hydrogen substituents selected from halo, haloalkyl, substituted or unsubstituted alkoxy, and cyano.

In an exemplary embodiment, the compounds of the invention used to treat chronic cough or itching have a structure according to Formula I, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, R$^1$ is of the formula:

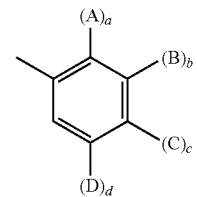

wherein A, B, C and D are independently selected from "aryl group substituents"; and the indices a, b, c, and d are independently selected from 0 and 1.

In an exemplary embodiment, the compounds of the invention used to treat chronic cough or itching have a structure according to Formula I, wherein R$^2$, R$^3$, R$^4$, R$^5$, R$^6$, R$^7$, R$^8$, R$^9$, R$^{10}$, R$^{11}$, R$^{12}$, R$^{13}$, and X are as described herein, A, B, C and D are independently selected from CN, Cl, Br, F, substituted or unsubstituted C$_1$-C$_6$ alkyl, substituted or unsubstituted C$_1$-C$_6$ heteroalkyl, substituted or unsubstituted C$_1$-C$_6$ haloalkyl, and substituted or unsubstituted C$_1$-C$_6$ alkoxy.

In an exemplary embodiment, wherein R$^1$, R$^3$, R$^4$, R$^5$, R$^6$, R$^7$, R$^8$, R$^9$, R$^{10}$, R$^{11}$, R$^{12}$, R$^{13}$, and X are as described herein, R$^2$ is selected from C$_1$-C$_{10}$ straight chain or branched substituted or unsubstituted C$_1$-C$_6$ alkyl, and C$_1$-C$_{10}$ substituted or unsubstituted C$_1$-C$_6$ alkyl heteroalkyl. In an exemplary embodiment, wherein R$^1$, R$^3$, R$^4$, R$^5$, R$^6$, R$^7$, R$^8$, R$^9$, R$^{10}$, R$^{11}$, R$^{12}$, R$^{13}$, and X are as described herein, R$^2$ includes substituted alkyl or substituted heteroalkyl groups, which are substituted with amide, oxo, substituted or unsubstituted aryl or substituted or unsubstituted heterocycloalkyl. Exemplary substituted aryl groups include substituted or unsubstituted phenyl, and an exemplary heterocycloalkyl moiety is an oxygen-containing heterocycle.

In an exemplary embodiment, a compound of the invention used to treat chronic cough or itching has the formula:

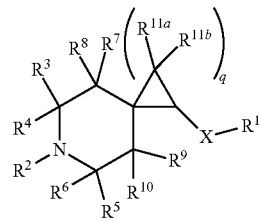

wherein $R^1$, $R^2$, $R^3$, $R^4$, $R^5$, $R^6$, $R^7$, $R^8$, $R^9$, $R^{10}$, $R^{11a}$, $R^{11b}$, and X are as described herein, wherein q is an integer selected from 1, 2, 3, 4 and 5. In an exemplary embodiment, wherein $R^1$, $R^2$, $R^3$, $R^4$, $R^5$, $R^6$, $R^7$, $R^8$, $R^9$, $R^{10}$, and X are as described herein, wherein $R^{11a}$ and $R^{11b}$ are members each independently selected from H, methyl, and fluorine. In an exemplary embodiment, wherein $R^1$, $R^2$, $R^3$, $R^4$, $R^5$, $R^6$, $R^7$, $R^8$, $R^9$, $R^{10}$, and X are as described herein, q is 1, $R^{11a}$ is H and $R^{11b}$ is F. In an exemplary embodiment, wherein $R^1$, $R^2$, $R^3$, $R^4$, $R^5$, $R^6$, $R^7$, $R^8$, $R^9$, $R^{10}$, and X are as described herein, q is 1, $R^{11a}$ is F and $R^{11b}$ is F.

In an exemplary embodiment, a compound of the invention used to treat chronic cough or itching has the formula:

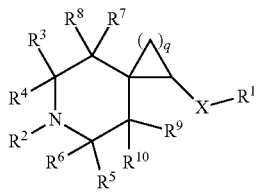

wherein $R^1$, $R^2$, $R^3$, $R^4$, $R^5$, $R^6$, $R^7$, $R^8$, $R^9$, $R^{10}$, and X are as described herein, q is an integer selected from 1, 2, 3, 4 and 5.

In an exemplary embodiment, a compound of the invention used to treat chronic cough or itching has the formula:

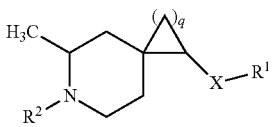

wherein X, $R^1$, and $R^2$ are as described herein, and q is 1 or 2.

In an exemplary embodiment, a compound of the invention used to treat chronic cough or itching has the formula:

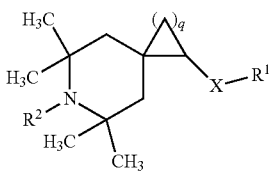

wherein X, $R^1$, and $R^2$ are as described herein, and q is 1 or 2.

In an exemplary embodiment, a compound of the invention used to treat chronic cough or itching has the formula:

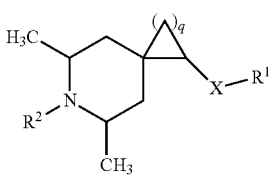

wherein X, $R^1$, and $R^2$ are as described herein, and q is 1 or 2.

In an exemplary embodiment, a compound of the invention used to treat chronic cough or itching has the formula:

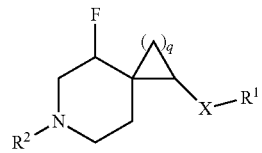

wherein X, $R^1$, and $R^2$ are as described herein, and q is 1 or 2.

In an exemplary embodiment, a compound of the invention used to treat chronic cough or itching has the formula:

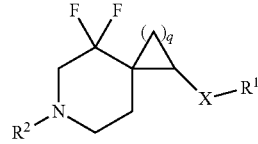

wherein X, $R^1$, and $R^2$ are as described herein, and q is 1 or 2.

In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted or unsubstituted benzyl or substituted or unsubstituted adamantyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted phenyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is unsubstituted phenyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is substituted or unsubstituted adamantyl. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is

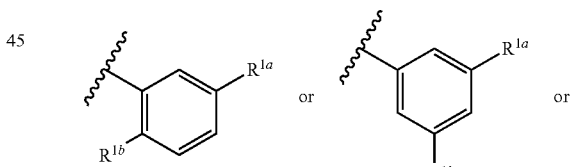

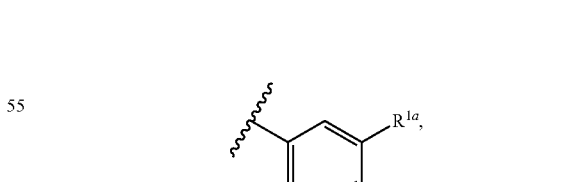

wherein ⁂ represents the covalent link between $R^1$ and X; and $R^{1a}$ and $R^{1b}$ are members each independently selected from halo, haloalkyl, substituted or unsubstituted alkoxy, and cyano. In an exemplary embodiment, wherein q, $R^2$, $R^3$, $R^4$, $R^5$, $R^6$, $R^7$, $R^8$, $R^9$, $R^{10}$, and X are as described herein, wherein $R^1$ is

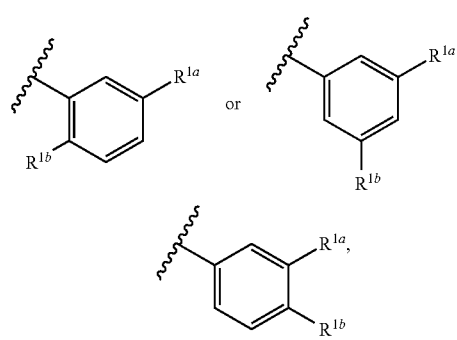

wherein ⸹ represents the covalent link between R¹ and X; and $R^{1a}$ and $R^{1b}$ are members each independently selected from F, Cl, Br, $CF_3$, methoxy, methyl, and CN. In an exemplary embodiment, wherein q, $R^2$, $R^3$, $R^4$, $R^5$, $R^6$, $R^7$, $R^8$, $R^9$, $R^{10}$, and X are as described herein, wherein R¹ is

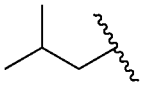

wherein ⸹ represents the covalent link between R¹ and X; and $R^{1a}$ and $R^{1b}$ are members each independently selected from F, Cl, and $CF_3$.

In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is substituted or unsubstituted alkyl. In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is substituted or unsubstituted heteroalkyl. In an exemplary embodiment, wherein q, $R^2$, $R^3$, $R^4$, $R^5$, $R^6$, $R^7$, $R^8$, $R^9$, $R^{10}$, and X are as described herein, wherein $R^2$ is

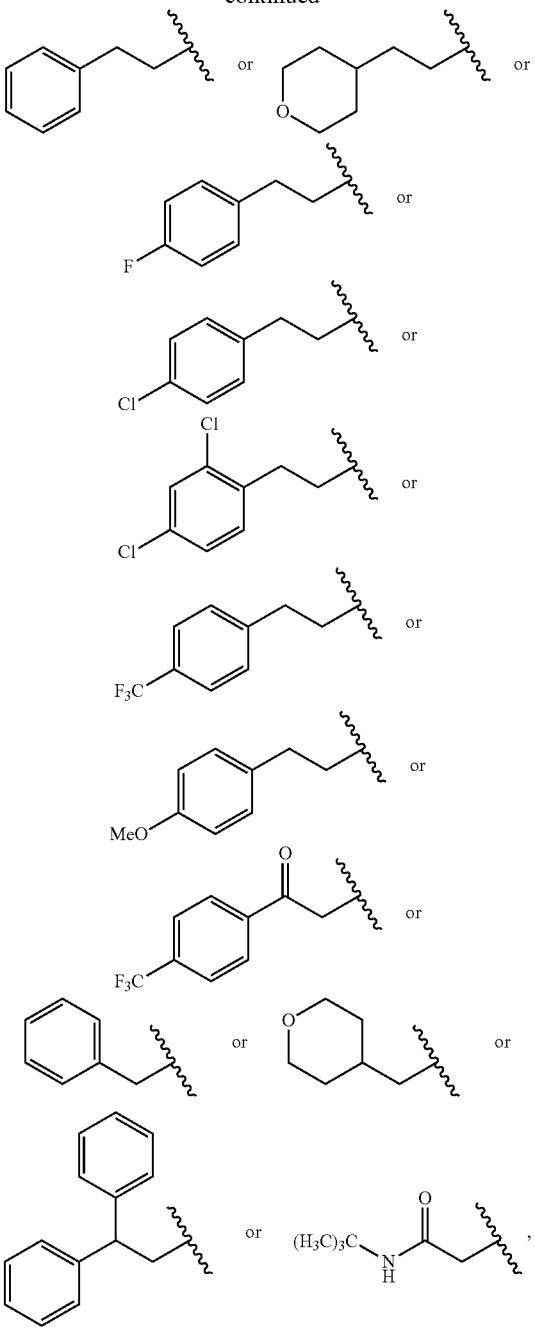

wherein ⸹ represents the covalent link between $R^2$ and the piperidine nitrogen.

In an exemplary embodiment, the compound used to treat chronic cough or itching has the following formula:

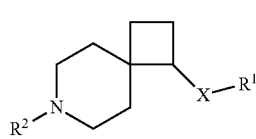

wherein X, $R^2$, and R¹ are as described herein.

In an exemplary embodiment, the compound used to treat chronic cough or itching has the following formula:

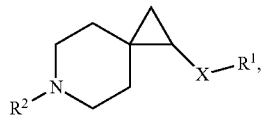

wherein X, R² , and R¹ are as described herein. In an exemplary embodiment, the compound is according to a formula described herein, and R¹ is phenyl substituted with one to three substituents, each of which is a member selected from the group consisting of F, Cl, and CF₃. In an exemplary embodiment, the compound is according to a formula described herein, and R¹ is phenyl substituted with one substituent which is a member selected from the group consisting of F, Cl, and CF₃. In an exemplary embodiment, the compound is according to a formula described herein, and R¹ is phenyl substituted with two substituents which are members each individually selected from the group consisting of F, Cl, and CF₃. In an exemplary embodiment, the compound is according to a formula described herein, and R¹ is phenyl substituted with thee substituents which are members each individually selected from the group consisting of F, Cl, and CF₃. In an exemplary embodiment, the compound has the following formula:

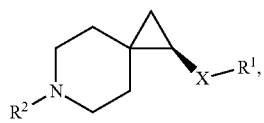

wherein X, R² , and R¹ are as described herein. In an exemplary embodiment, the compound has the following formula:

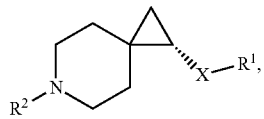

wherein X, R² , and R¹ are as described herein.

In an exemplary embodiment, the compound used to treat chronic cough or itching is

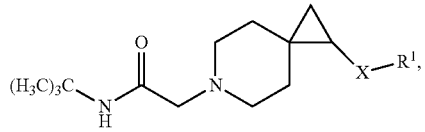

wherein X and R¹ are as described herein. In an exemplary embodiment, the compound is

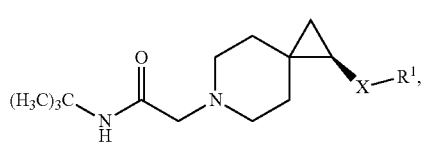

wherein X and R¹ are as described herein. In an exemplary embodiment, the compound is

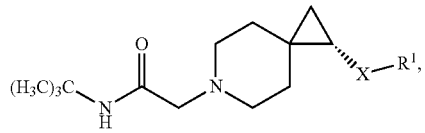

wherein X and R¹ are as described herein. In an exemplary embodiment, the compound is

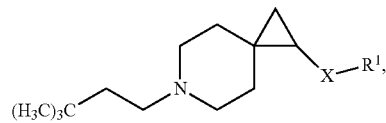

wherein X and R¹ are as described herein. In an exemplary embodiment, the compound is

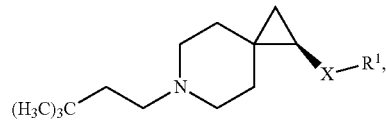

wherein X and R¹ are as described herein. In an exemplary embodiment, the compound is

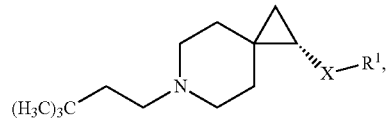

wherein X and R¹ are as described herein.

In an exemplary embodiment, the compound is

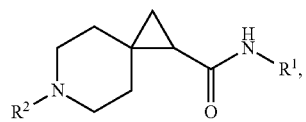

wherein R¹ and R² are as described herein. In an exemplary embodiment, the compound is

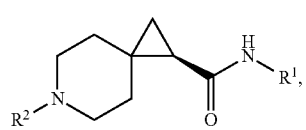

wherein R¹ and R² are as described herein. In an exemplary embodiment, the compound is

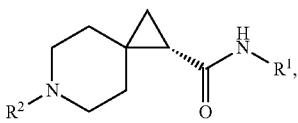

wherein $R^1$ and $R^2$ are as described herein. In an exemplary embodiment, the compound is

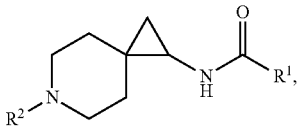

wherein $R^1$ and $R^2$ are as described herein. In an exemplary embodiment, the compound is

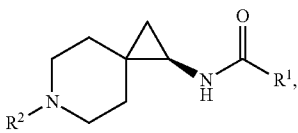

wherein $R^1$ and $R^2$ are as described herein. In an exemplary embodiment, the compound is

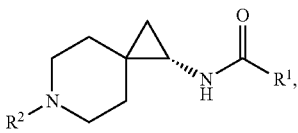

wherein $R^1$ and $R^2$ are as described herein.

In an exemplary embodiment, the compound is

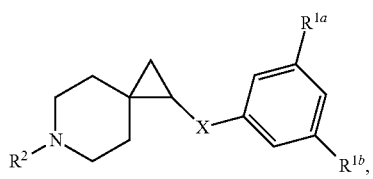

wherein X and $R^2$ are as described herein, $R^{1a}$ and $R^{1b}$ are members each independently selected from the group consisting of F, Cl, and $CF_3$.

In an exemplary embodiment, the compound is

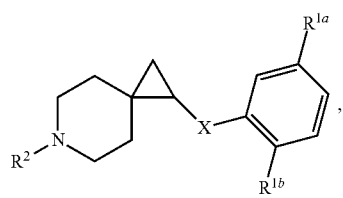

wherein X and $R^2$ are as described herein, $R^{1a}$ and $R^{1b}$ are members each independently selected from the group consisting of F, Cl, and $CF_3$.

In an exemplary embodiment, the compound is

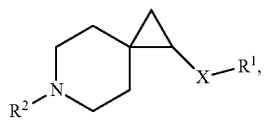

wherein X and $R^2$ are as described herein, $R^1$ is as described herein. In an exemplary embodiment, the compound is

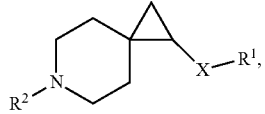

wherein X and $R^2$ are as described herein, $R^1$ is unsubstituted adamantyl. In an exemplary embodiment, the compound is

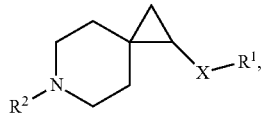

wherein X and $R^2$ are as described herein, $R^1$ is unsubstituted adamant-1-yl.

In an exemplary embodiment, the compound is

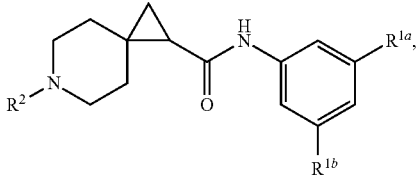

wherein $R^2$, $R^{1a}$ and $R^{1b}$ are as described herein. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ is as described herein, and $R^{1b}$ is F. In an exemplary embodiment, the compound is according to a formula described herein which contains $R^{1a}$ and $R^{1b}$, wherein $R^{1a}$ is as described herein, and $R^{1b}$ is Cl. In an exemplary embodiment, the compound is according to a formula described herein which contains $R^{1a}$ and $R^{1b}$, wherein $R^{1a}$ is as described herein, and $R^{1b}$ is $CF_3$. In an exemplary embodiment, the compound is according to a formula described herein which contains $R^{1a}$ and $R^{1b}$, wherein $R^{1b}$ is as described herein, and $R^{1a}$ is F. In an exemplary embodiment, the compound is according to a formula described herein which contains $R^{1a}$ and $R^{1b}$, wherein $R^{1b}$ is as described herein, and $R^{1a}$ is Cl. In an exemplary embodiment, the compound is according to a formula described herein which contains $R^{1a}$ and $R^{1b}$, wherein $R^{1b}$ is as described herein, and $R^{1a}$ is $CF_3$. In an exemplary embodiment, the compound is

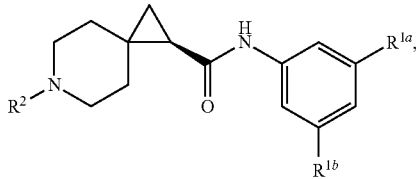

wherein $R^2$, $R^{1a}$ and $R^{1b}$ are as described herein. In an exemplary embodiment, the compound is

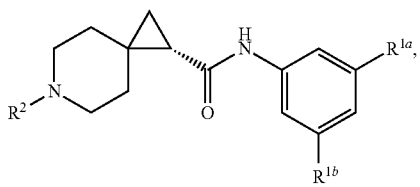

wherein $R^2$, $R^{1a}$ and $R^{1b}$ are as described herein. In an exemplary embodiment, the compound is

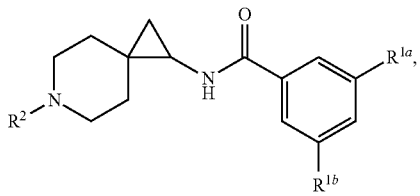

wherein $R^2$, $R^{1a}$ and $R^{1b}$ are as described herein. In an exemplary embodiment, the compound is

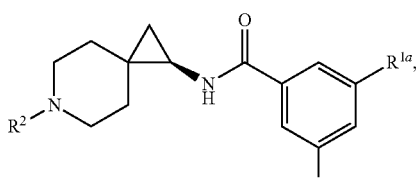

wherein $R^2$, $R^{1a}$ and $R^{1b}$ are as described herein. In an exemplary embodiment, the compound is

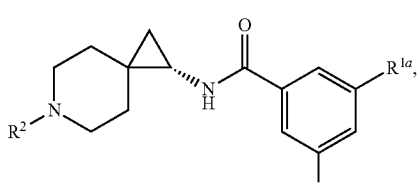

wherein $R^2$, $R^{1a}$ and $R^{1b}$ are as described herein.

In an exemplary embodiment, the compound is

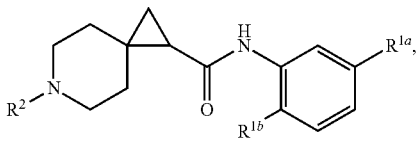

wherein $R^2$, $R^{1a}$ and $R^{1b}$ are as described herein. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ and $R^{1b}$ are members each independently selected from the group consisting of F, Cl, and $CF_3$. In an exemplary embodiment, the compound is according to a formula described herein which contains $R^{1a}$ and $R^{1b}$, wherein $R^{1a}$ is as described herein, and $R^{1b}$ is F. In an exemplary embodiment, the compound is according to a formula described herein which contains $R^{1a}$ and $R^{1b}$, wherein $R^{1a}$ is as described herein, and $R^{1b}$ is Cl. In an exemplary embodiment, the compound is according to a formula described herein which contains $R^{1a}$ and $R^{1b}$, wherein $R^{1a}$ is as described herein, and $R^{1b}$ is $CF_3$. In an exemplary embodiment, the compound is according to a formula described herein which contains $R^{1a}$ and $R^{1b}$, wherein $R^{1b}$ is as described herein, and $R^{1a}$ is F. In an exemplary embodiment, the compound is according to a formula described herein which contains $R^{1a}$ and $R^{1b}$, wherein $R^{1b}$ is as described herein, and $R^{1a}$ is Cl. In an exemplary embodiment, the compound is according to a formula described herein which contains $R^{1a}$ and $R^{1b}$, wherein $R^{1b}$ is as described herein, and $R^{1a}$ is $CF_3$. In an exemplary embodiment, the compound is

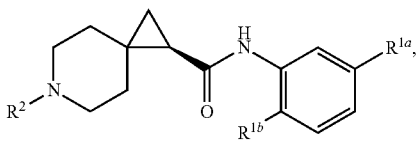

wherein $R^2$, $R^{1a}$ and $R^{1b}$ are as described herein. In an exemplary embodiment, the compound is

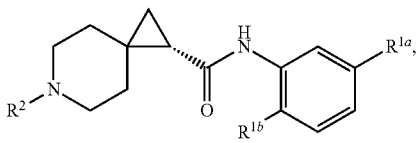

wherein $R^2$, $R^{1a}$ and $R^{1b}$ are as described herein. In an exemplary embodiment, the compound is

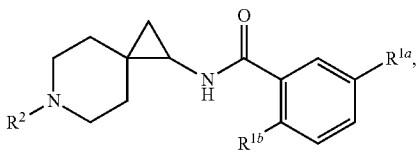

wherein $R^2$, $R^{1a}$ and $R^{1b}$ are as described herein. In an exemplary embodiment, the compound is

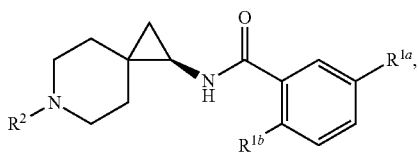

wherein $R^2$, $R^{1a}$ and $R^{1b}$ are as described herein. In an exemplary embodiment, the compound is

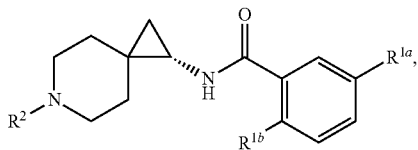

wherein $R^2$, $R^{1a}$ and $R^{1b}$ are as described herein.

In an exemplary embodiment, the compound is

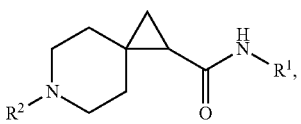

wherein $R^2$ is as described herein, and $R^1$ is unsubstituted adamantyl. In an exemplary embodiment, the compound is

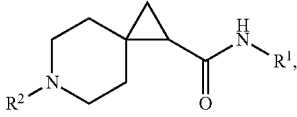

wherein $R^2$ is as described herein, and $R^1$ is unsubstituted adamant-1-yl. In an exemplary embodiment, the compound is

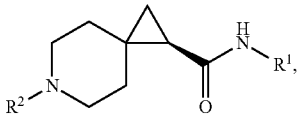

wherein $R^2$ is as described herein, and $R^1$ is unsubstituted adamantyl. In an exemplary embodiment, the compound is

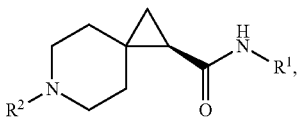

wherein $R^2$ is as described herein, and $R^1$ is unsubstituted adamant-1-yl. In an exemplary embodiment, the compound is

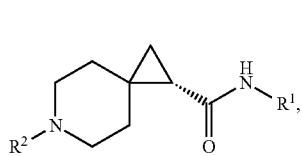

wherein $R^2$ is as described herein, and $R^1$ is unsubstituted adamantyl. In an exemplary embodiment, the compound is

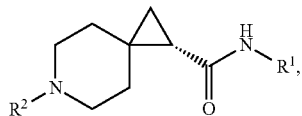

wherein $R^2$ is as described herein, and $R^1$ is unsubstituted adamant-1-yl.

In an exemplary embodiment, the compound is

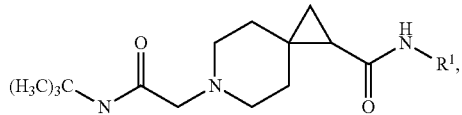

wherein $R^1$ is as described herein. In an exemplary embodiment, the compound is

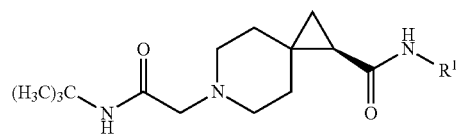

wherein $R^1$ is as described herein. In an exemplary embodiment, the compound is

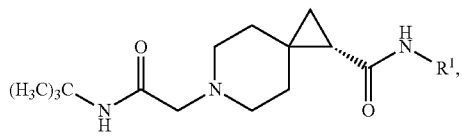

wherein $R^1$ is as described herein. In an exemplary embodiment, the compound is

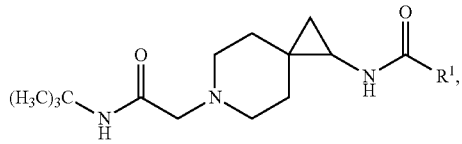

wherein $R^1$ is as described herein. In an exemplary embodiment, the compound is

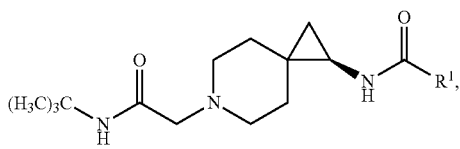

wherein R¹ is as described herein. In an exemplary embodiment, the compound is

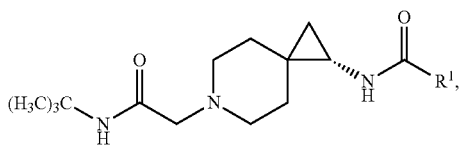

wherein R¹ is as described herein. In an exemplary embodiment, the compound is

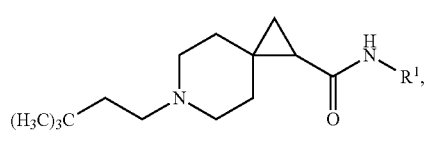

wherein R¹ is as described herein. In an exemplary embodiment, the compound is

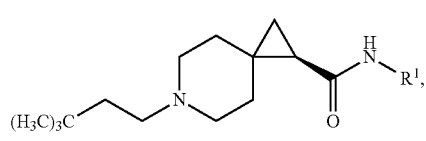

wherein R¹ is as described herein. In an exemplar embodiment, the compound is

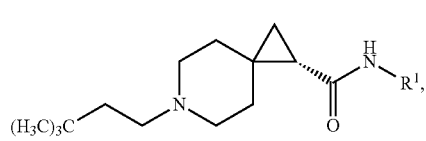

wherein R¹ is as described herein. In an exemplary embodiment, the compound is

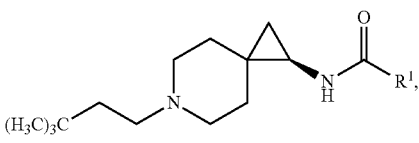

wherein R¹ is as described herein. In an exemplary embodiment, the compound is

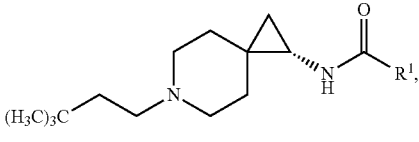

wherein R¹ is as described herein.

In an exemplary embodiment, the compound is

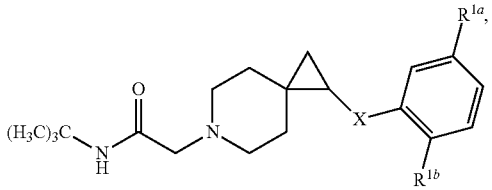

wherein X, $R^{1a}$ and $R^{1b}$ are as described herein. In an exemplary embodiment, the compound is

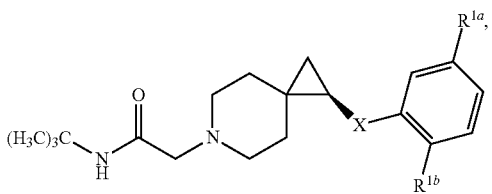

wherein X, $R^{1a}$ and $R^{1b}$ are as described herein. In an exemplary embodiment, the compound is

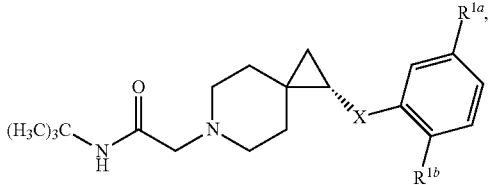

wherein X, $R^{1a}$ and $R^{1b}$ are as described herein.

In an exemplary embodiment, the compound is

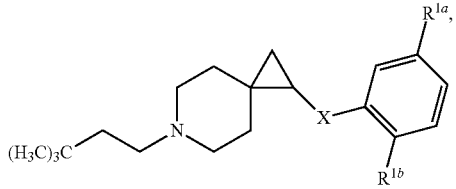

wherein X, $R^{1a}$ and $R^{1b}$ are as described herein. In an exemplary embodiment, the compound is

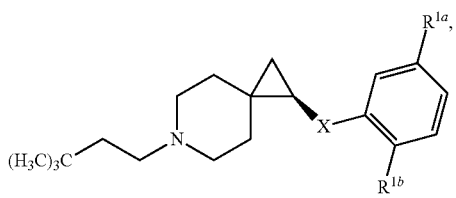

wherein X, $R^{1a}$ and $R^{1b}$ are as described herein. In an exemplary embodiment, the compound is

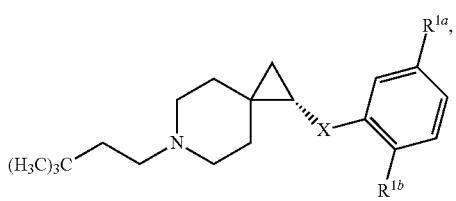

wherein X, $R^{1a}$ and $R^{1b}$ are as described herein.

In an exemplary embodiment, the compound is

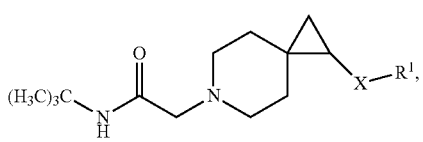

wherein X is as described herein, and $R^1$ is unsubstituted adamantyl. In an exemplary embodiment, the compound is

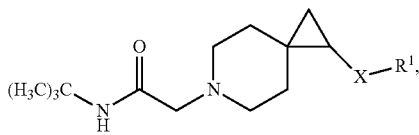

wherein X is as described herein, and $R^1$ is unsubstituted adamant-1-yl. In an exemplary embodiment, the compound is

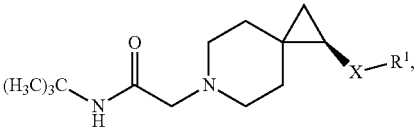

wherein X is as described herein, and $R^1$ is unsubstituted adamantyl. In an exemplary embodiment, the compound is

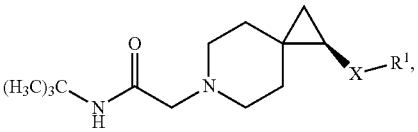

wherein X is as described herein, and $R^1$ is unsubstituted adamant-1-yl. In an exemplary embodiment, the compound is

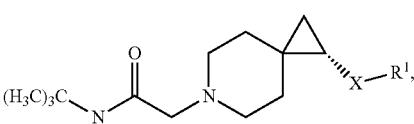

wherein X is as described herein, and $R^1$ is unsubstituted adamantyl. In an exemplary embodiment, the compound is

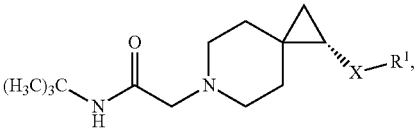

wherein X is as described herein, and $R^1$ is unsubstituted adamant-1-yl. In an exemplary embodiment, the compound is

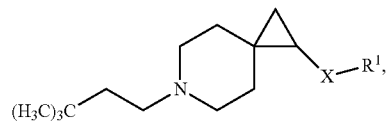

wherein X is as described herein, and $R^1$ is unsubstituted adamant-1-yl. In an exemplary embodiment, the compound is

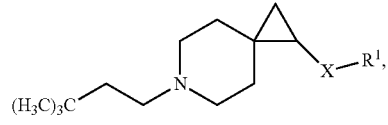

wherein X is as described herein, and $R^1$ is unsubstituted adamantyl. In an exemplary embodiment, the compound is

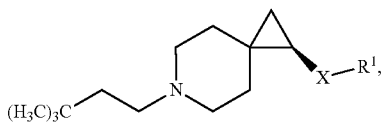

wherein X is as described herein, and R¹ is unsubstituted adamantyl. In an exemplary embodiment, the compound is

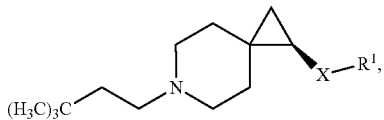

wherein X is as described herein, and R¹ is unsubstituted adamant-1-yl. In an exemplary embodiment, the compound is

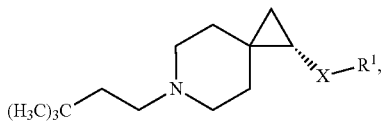

wherein X is as described herein, and R¹ is unsubstituted adamantyl. In an exemplary embodiment, the compound is

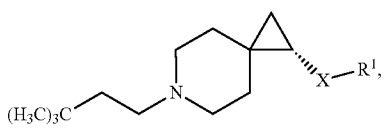

wherein X is as described herein, and R¹ is unsubstituted adamant-1-yl.

In an exemplary embodiment, the compound is

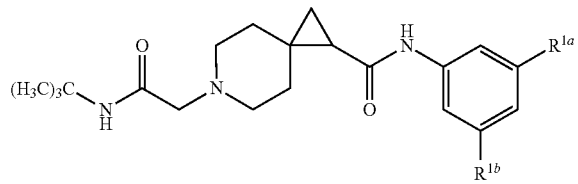

wherein $R^{1a}$ and $R^{1b}$ are members each independently selected from the group consisting of F, Cl, and $CF_3$. In an exemplary embodiment, the compound is

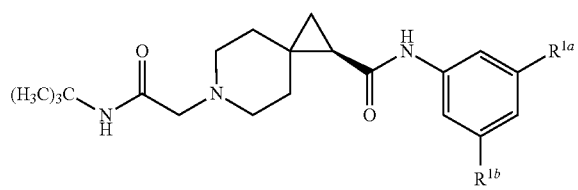

wherein $R^{1a}$ and $R^{1b}$ are members each independently selected from the group consisting of F, Cl, and $CF_3$. In an exemplary embodiment, the compound is

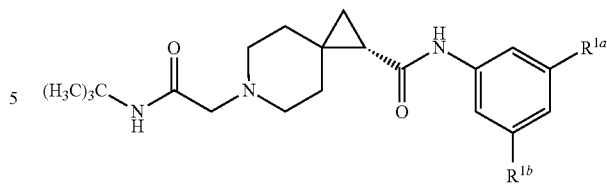

wherein $R^{1a}$ and $R^{1b}$ are members each independently selected from the group consisting of F, Cl, and $CF_3$. In an exemplary embodiment, the compound is

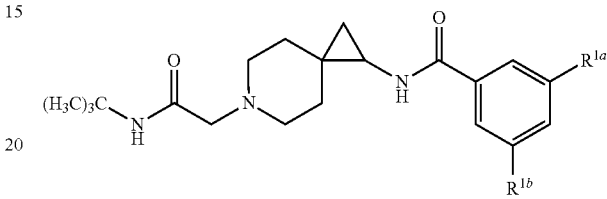

wherein $R^{1a}$ and $R^{1b}$ are members each independently selected from the group consisting of F, Cl, and $CF_3$. In an exemplary embodiment, the compound is

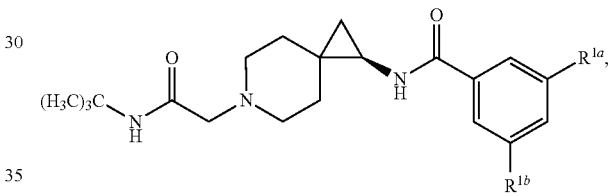

wherein $R^{1a}$ and $R^{1b}$ are members each independently selected from the group consisting of F, Cl, and $CF_3$. In an exemplary embodiment, the compound is

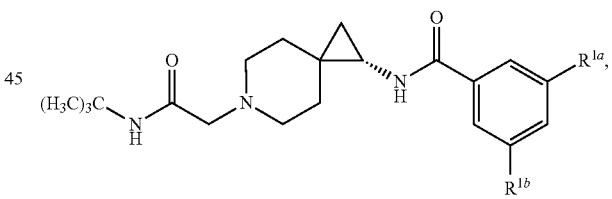

wherein $R^{1a}$ and $R^{1b}$ are members each independently selected from the group consisting of F, Cl, and $CF_3$. In an exemplary embodiment, the compound is

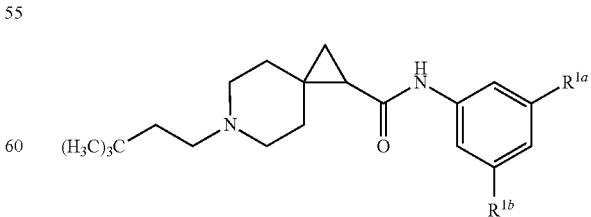

wherein $R^{1a}$ and $R^{1b}$ are members each independently selected from the group consisting of F, Cl, and $CF_3$. In an exemplary embodiment, the compound is

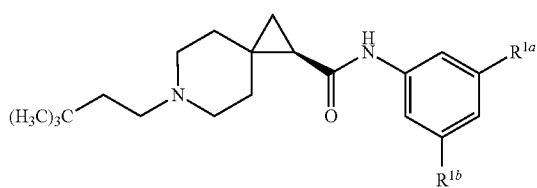

wherein $R^{1a}$ and $R^{1b}$ are members each independently selected from the group consisting of F, Cl, and $CF_3$. In an exemplary embodiment, the compound is

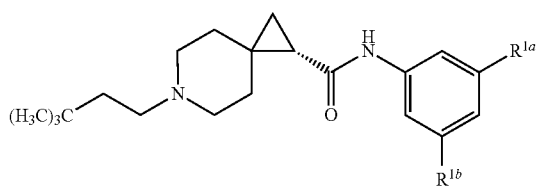

wherein $R^{1a}$ and $R^{1b}$ are members each independently selected from the group consisting of F, Cl, and $CF_3$.

In an exemplary embodiment, the compound is

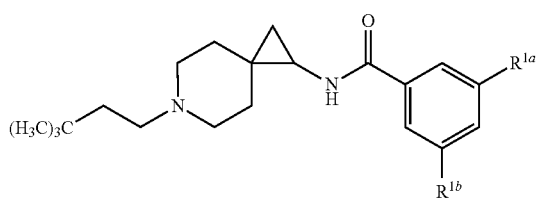

wherein $R^{1a}$ and $R^{1b}$ are members each independently selected from the group consisting of F, Cl, and $CF_3$. In an exemplary embodiment, the compound is

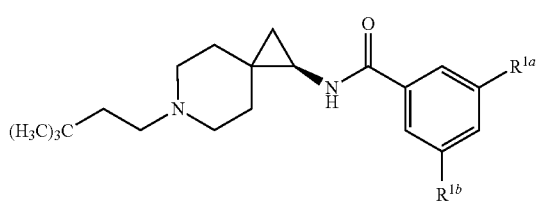

wherein $R^{1a}$ and $R^{1b}$ are members each independently selected from the group consisting of F, Cl, and $CF_3$. In an exemplary embodiment, the compound is

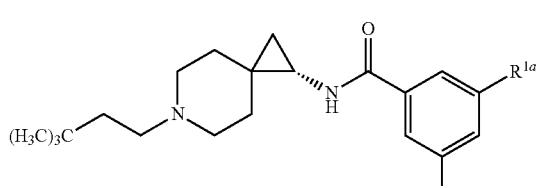

wherein $R^{1a}$ and $R^{1b}$ are members each independently selected from the group consisting of F, Cl, and $CF_3$.

In an exemplary embodiment, the compound is

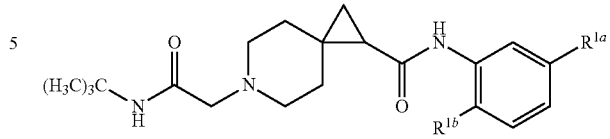

wherein $R^{1a}$ and $R^{1b}$ are members each independently selected from the group consisting of F, Cl, and $CF_3$. In an exemplary embodiment, the compound is

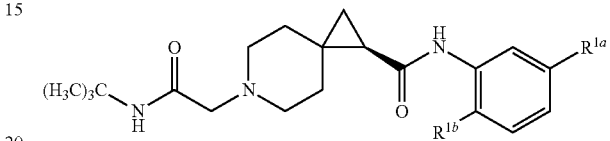

wherein $R^{1a}$ and $R^{1b}$ are members each independently selected from the group consisting of F, Cl, and $CF_3$. In an exemplary embodiment, the compound is

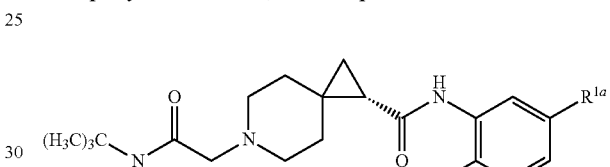

wherein $R^{1a}$ and $R^{1b}$ are members each independently selected from the group consisting of F, Cl, and $CF_3$. In an exemplary embodiment, the compound is

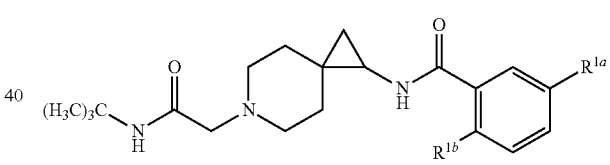

wherein $R^{1a}$ and $R^{1b}$ are members each independently selected from the group consisting of F, Cl, and $CF_3$. In an exemplary embodiment, the compound is

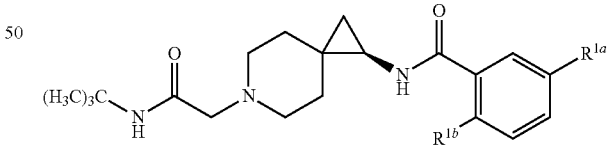

wherein $R^{1a}$ and $R^{1b}$ are members each independently selected from the group consisting of F, Cl, and $CF_3$. In an exemplary embodiment, the compound is

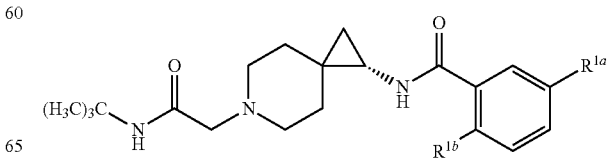

wherein $R^{1a}$ and $R^{1b}$ are members each independently selected from the group consisting of F, Cl, and CF$_3$. In an exemplary embodiment, the compound is

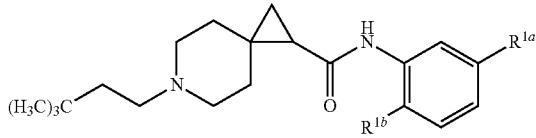

wherein $R^{1a}$ and $R^{1b}$ are members each independently selected from the group consisting of F, Cl, and CF$_3$. In an exemplary embodiment, the compound is

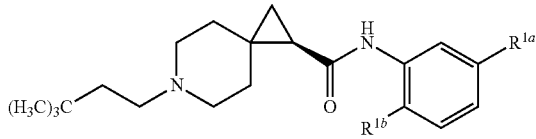

wherein $R^{1a}$ and $R^{1b}$ are members each independently selected from the group consisting of F, Cl, and CF$_3$. In an exemplary embodiment, the compound is

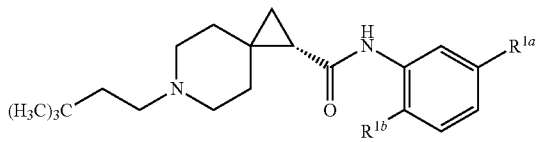

wherein $R^{1a}$ and $R^{1b}$ are members each independently selected from the group consisting of F, Cl, and CF$_3$. In an exemplary embodiment, the compound is

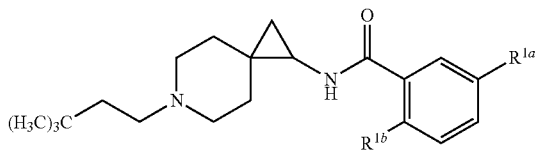

wherein $R^{1a}$ and $R^{1b}$ are members each independently selected from the group consisting of F, Cl, and CF$_3$. In an exemplary embodiment, the compound is

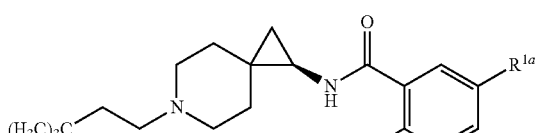

wherein $R^{1a}$ and $R^{1b}$ are members each independently selected from the group consisting of F, Cl, and CF$_3$. In an exemplary embodiment, the compound is

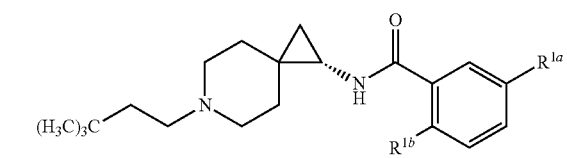

wherein $R^{1a}$ and $R^{1b}$ are members each independently selected from the group consisting of F, Cl, and CF$_3$.

In an exemplary embodiment, the compound is

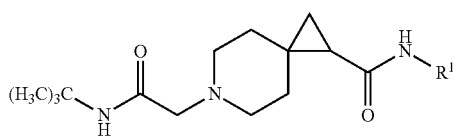

wherein $R^1$ is unsubstituted adamantyl. In an exemplary embodiment, the compound is

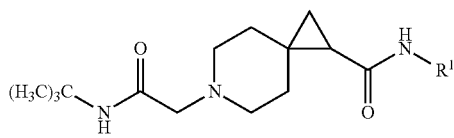

wherein $R^1$ is unsubstituted adamant-1-yl. In an exemplary embodiment, the compound is

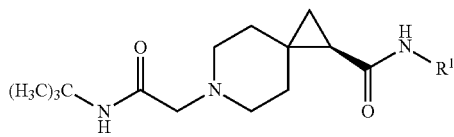

wherein $R^1$ is unsubstituted adamantyl. In an exemplary embodiment, the compound is

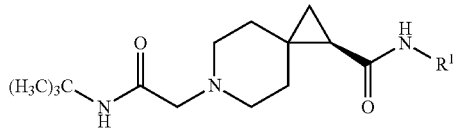

wherein $R^1$ is unsubstituted adamant-1-yl. In an exemplary embodiment, the compound is

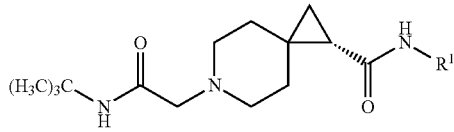

wherein $R^1$ is unsubstituted adamantyl. In an exemplary embodiment, the compound is

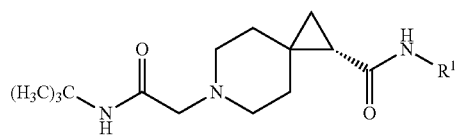

wherein R¹ is unsubstituted adamant-1-yl. In an exemplary embodiment, the compound is

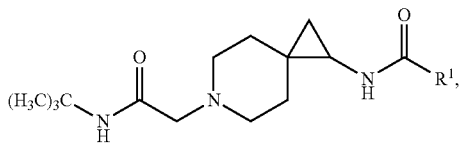

wherein R¹ is unsubstituted adamantyl. In an exemplary embodiment, the compound is

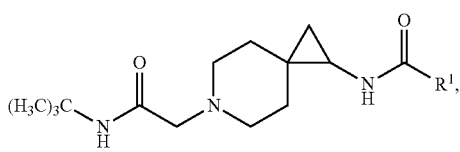

wherein R¹ is unsubstituted adamant-1-yl.
In an exemplary embodiment, the compound is

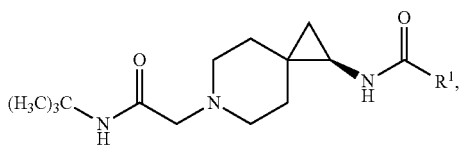

wherein R¹ is unsubstituted adamantyl. In an exemplary embodiment, the compound is

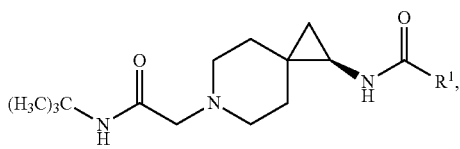

wherein R¹ is unsubstituted adamant-1-yl.
In an exemplary embodiment, the compound is

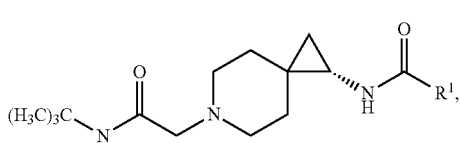

wherein R¹ is unsubstituted adamantyl. In an exemplary embodiment, the compound is

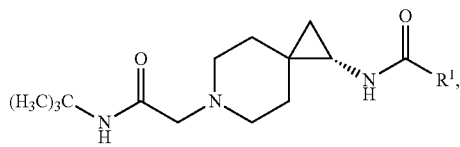

wherein R¹ is unsubstituted adamant-1-yl.
In an exemplary embodiment, the compound is

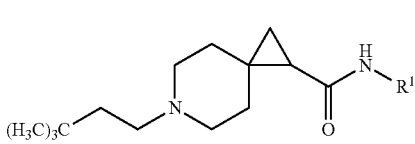

wherein R¹ is unsubstituted adamantyl. In an exemplary embodiment, the compound is

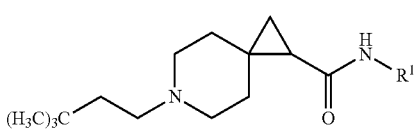

wherein R¹ is unsubstituted adamant-1-yl. In an exemplary embodiment, the compound is

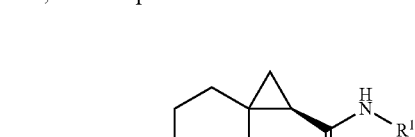

wherein R¹ is unsubstituted adamantyl. In an exemplary embodiment, the compound is

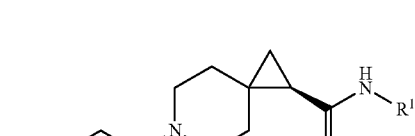

wherein R¹ is unsubstituted adamant-1-yl.
In an exemplary embodiment, the compound is

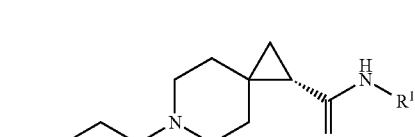

wherein R¹ is unsubstituted adamantyl. In an exemplary embodiment, the compound is

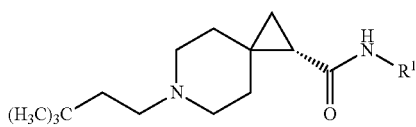

wherein R¹ is unsubstituted adamant-1-yl. In an exemplary embodiment, the compound is

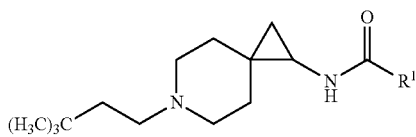

wherein R¹ is unsubstituted adamantyl. In an exemplary embodiment, the compound is

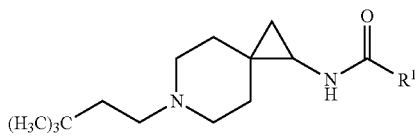

wherein R¹ is unsubstituted adamant-1-yl. In an exemplary embodiment, the compound is

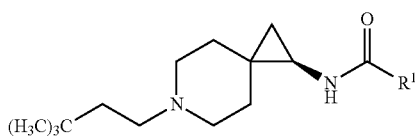

wherein R¹ is unsubstituted adamantyl. In an exemplary embodiment, the compound is

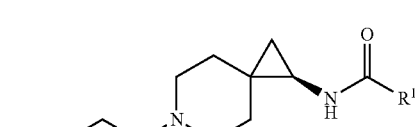

wherein R¹ is unsubstituted adamant-1-yl. In an exemplary embodiment, the compound is

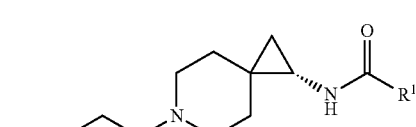

wherein R¹ is unsubstituted adamantyl. In an exemplary embodiment, the compound is

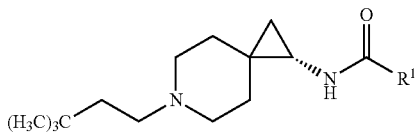

wherein R¹ is unsubstituted adamant-1-yl.

In an exemplary embodiment, the compound is

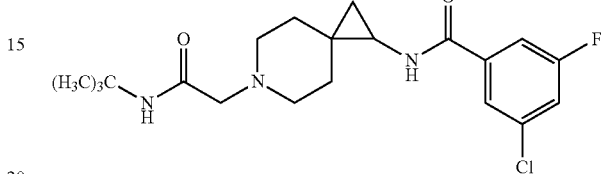

or a pharmaceutically acceptable salt thereof. In an exemplary embodiment, the compound is

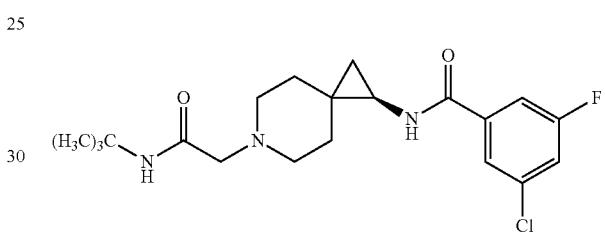

or a pharmaceutically acceptable salt thereof. In an exemplary embodiment, the compound is

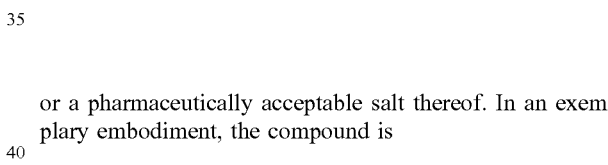

or a pharmaceutically acceptable salt thereof.

In an exemplary embodiment, the compound is

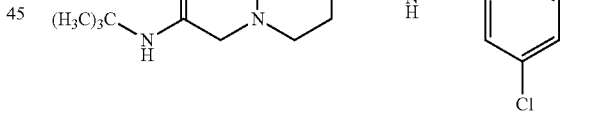

or a pharmaceutically acceptable salt thereof.

In an exemplary embodiment, the compound is

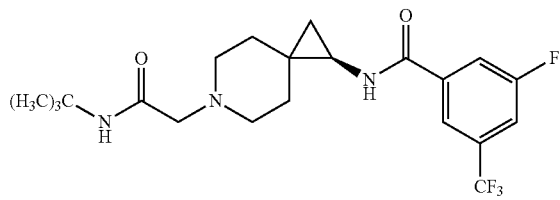 [SMILES: "(H3C)3C" ; NC(=O)CN1CCC2(CC1)C[C@H]2NC(=O)c1cc(F)cc(C(F)(F)F)c1]

or a pharmaceutically acceptable salt thereof. In an exemplary embodiment, the compound is

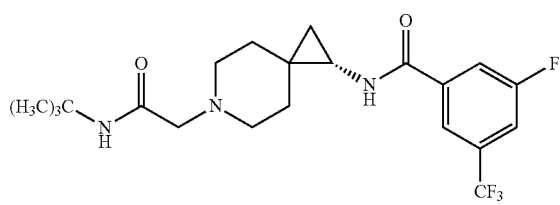 [SMILES: "(H3C)3C" ; NC(=O)CN1CCC2(CC1)C[C@@H]2NC(=O)c1cc(F)cc(C(F)(F)F)c1]

or a pharmaceutically acceptable salt thereof.

In an exemplary embodiment, the compound is

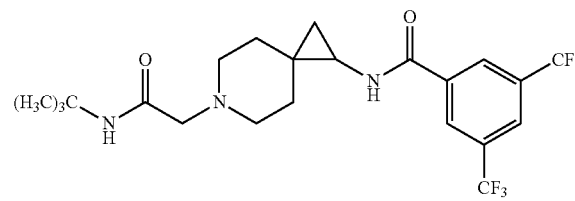

or a pharmaceutically acceptable salt thereof. In an exemplary embodiment, the compound is

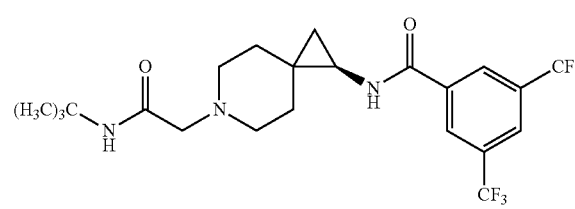

or a pharmaceutically acceptable salt thereof. In an exemplary embodiment, the compound is

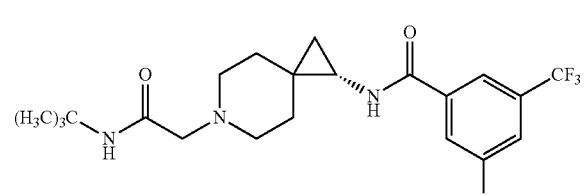

or a pharmaceutically acceptable salt thereof.

In an exemplary embodiment, the compound is

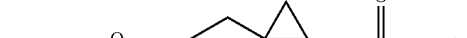

or a pharmaceutically acceptable salt thereof. In an exemplary embodiment, the compound is

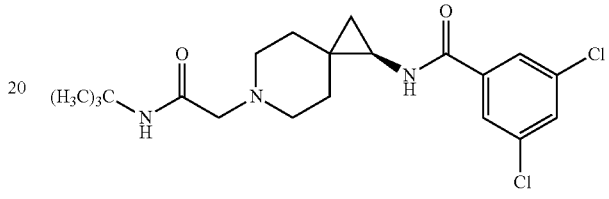

or a pharmaceutically acceptable salt thereof. In an exemplary embodiment, the compound is

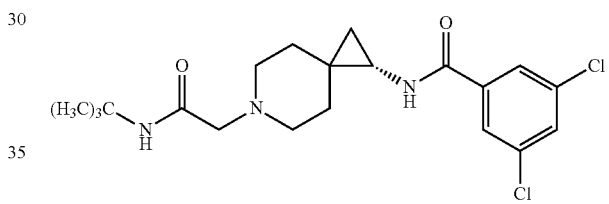

or a pharmaceutically acceptable salt thereof.

In an exemplary embodiment, the compound is

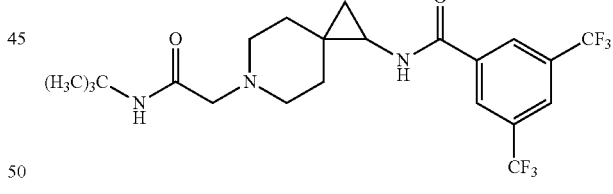

or a pharmaceutically acceptable salt thereof. In an exemplary embodiment, the compound is

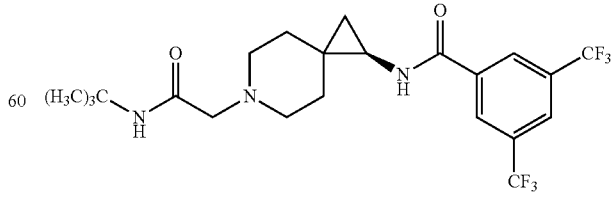

or a pharmaceutically acceptable salt thereof. In an exemplary embodiment, the compound is

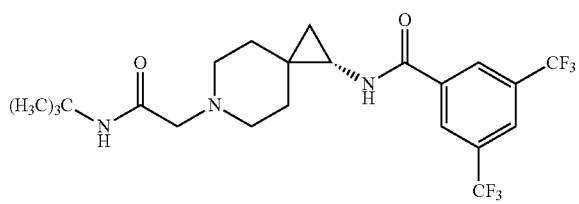

or a pharmaceutically acceptable salt thereof.

In an exemplary embodiment, the compound is

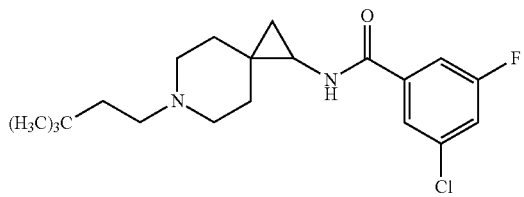 [SMILES: CC(C)(C)CCN1CCC2(CC1)CC2NC(=O)c1cc(F)cc(Cl)c1]

or a pharmaceutically acceptable salt thereof. In an exemplary embodiment, the compound is

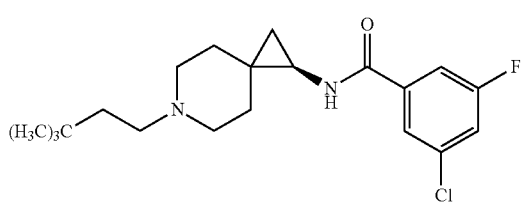 [SMILES: CC(C)(C)CCN1CCC2(CC1)C[C@H]2NC(=O)c1cc(F)cc(Cl)c1]

or a pharmaceutically acceptable salt thereof. In an exemplary embodiment, the compound is

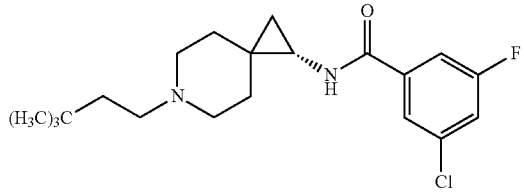 [SMILES: CC(C)(C)CCN1CCC2(CC1)C[C@@H]2NC(=O)c1cc(F)cc(Cl)c1]

or a pharmaceutically acceptable salt thereof.

In an exemplary embodiment, the compound is

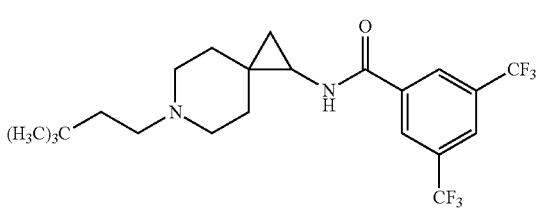 [SMILES: CC(C)(C)CCN1CCC2(CC1)CC2NC(=O)c1cc(C(F)(F)F)cc(C(F)(F)F)c1]

or a pharmaceutically acceptable salt thereof. In an exemplary embodiment, the compound is

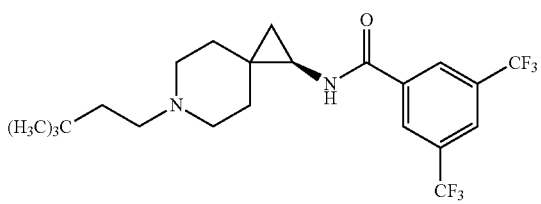 [SMILES: CC(C)(C)CCN1CCC2(CC1)C[C@H]2NC(=O)c1cc(C(F)(F)F)cc(C(F)(F)F)c1]

or a pharmaceutically acceptable salt thereof. In an exemplary embodiment, the compound is

[Second column structures: 3,5-CF3 variant, then N-tBu amide with 3-CF3-5-F, then similar variant, then final structure]

or a pharmaceutically acceptable salt thereof.

In an exemplary embodiment, the compound is or a pharmaceutically acceptable salt thereof. In an exemplary embodiment, the compound is or a pharmaceutically acceptable salt thereof. In an exemplary embodiment, the compound is or a pharmaceutically acceptable salt thereof.

In an exemplary embodiment, the compound is

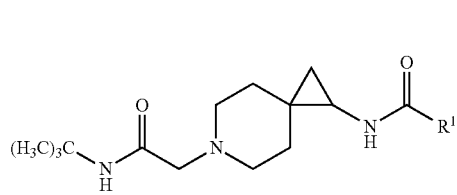

or a pharmaceutically acceptable salt thereof, wherein R¹ is unsubstituted adamant-1-yl. In an exemplary embodiment, the compound is

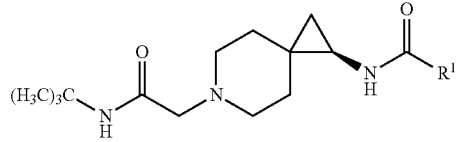

or a pharmaceutically acceptable salt thereof, wherein R¹ is unsubstituted adamant-1-yl. In an exemplary embodiment, the compound is

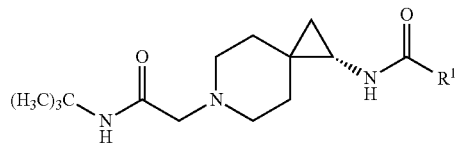

or a pharmaceutically acceptable salt thereof, wherein R¹ is unsubstituted adamant-1-yl.

In an exemplary embodiment, the compound is

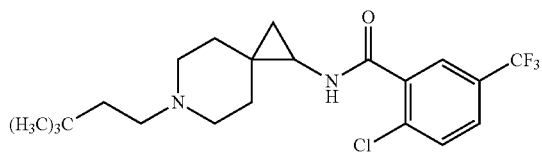 [SMILES: CC(C)(C)CCN1CCC2(CC1)CC2NC(=O)c1cc(C(F)(F)F)ccc1Cl]

or a pharmaceutically acceptable salt thereof. In an exemplary embodiment, the compound is

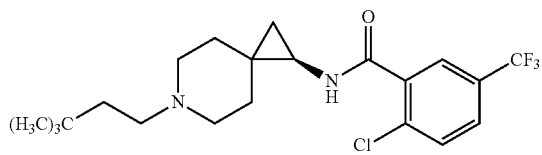 [SMILES: CC(C)(C)CCN1CCC2(CC1)C[C@H]2NC(=O)c1cc(C(F)(F)F)ccc1Cl]

or a pharmaceutically acceptable salt thereof. In an exemplary embodiment, the compound is

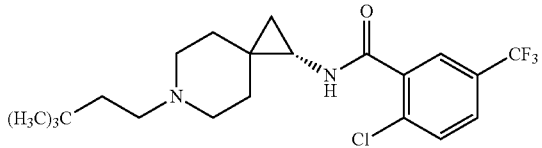 [SMILES: CC(C)(C)CCN1CCC2(CC1)C[C@@H]2NC(=O)c1cc(C(F)(F)F)ccc1Cl]

or a pharmaceutically acceptable salt thereof.

In one exemplary embodiment, the structure of AFA-358 is

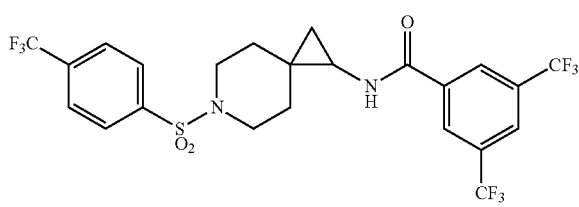 [SMILES: O=C(NC1CC12CCN(S(=O)(=O)c1ccc(C(F)(F)F)cc1)CC2)c1cc(C(F)(F)F)cc(C(F)(F)F)c1]

In one exemplary embodiment, the structure of AFA-309 is

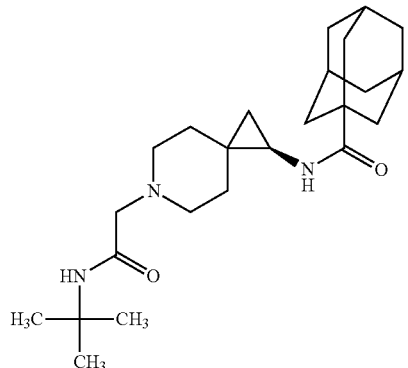

In one exemplary embodiment, the structure of AFA-258 (Z944 from Zalicus) is

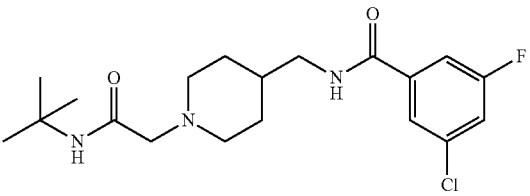 [SMILES: CC(C)(C)NC(=O)CN1CCC(CNC(=O)c2cc(F)cc(Cl)c2)CC1]

In one exemplary embodiment, the structure of AFA-353 is

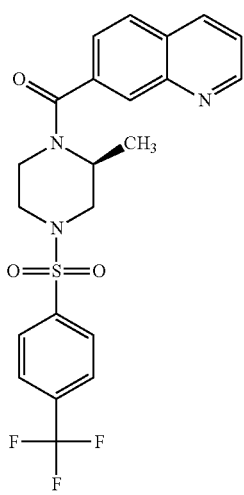 [SMILES: C[C@H]1CN(S(=O)(=O)c2ccc(C(F)(F)F)cc2)CCN1C(=O)c1ccc2cccnc2c1]

AFA-309, 353 and 358 are novel T-type $Ca_{v3}$ channel modulators used in the treatment of pathological conditions, including pain, hypersensitive cough and itching.

The invention also provides a pharmaceutical formulation comprising a therapeutically effective amount of a compound according to Formula I or individually disclosed herein. The formulation further includes a pharmaceutically acceptable carrier.

The invention also provides a method for treating hypersensitive cough or itching responsive to selective inhibition of the T Channel known as the $Ca_{v3.2}$ channel comprising administering to a mammal a therapeutically effective amount of a compound according to Formula I or individually disclosed herein.

The present invention provides compounds which are selective T-Channel inhibitory compounds useful for relief of hypersensitive cough or itching.

The invention also includes, where chemically possible, all stereoisomers and geometric isomers of the compounds, including diastereomers, enantiomers, and cis/trans (E/Z) isomers. The invention also includes mixtures of stereoisomers and/or geometric isomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention. Unless a specific isotope is indicated, the invention includes all isotopologues of the compounds disclosed herein, such as, for example, deuterated derivatives of the compounds (where H can be $^2H$, i.e., D).

In the context of the present invention, compounds that are considered to possess activity as T-Channel inhibitors are those displaying 50% inhibition of the $Ca^{++}$ voltage ($IC_{50}$) at a concentration of not higher than about 100 µM, preferably, not higher than about 10 µM, more preferably not higher than about 1 µM and most preferably not higher than about 100 nM.

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as "Greene's Protective Groups in Organic Synthesis: Fifth Edition" by Peter G. M. Wuts, [John Wiley & Sons, New York, 2014], DOI: 10.1002/9781118905074, which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

Pharmaceutical Formulations

The present invention further provides pharmaceutical formulations comprising as active agents, the compounds described herein.

In an exemplary embodiment, the invention is a pharmaceutical formulation comprising a therapeutically effective amount of a compound described herein, or a pharmaceutically acceptable salt thereof. In an exemplary embodiment, the invention is a pharmaceutical formulation comprising a therapeutically effective amount of a compound of a formula described herein, or a pharmaceutically acceptable salt thereof.

In an exemplary embodiment, the invention is a pharmaceutical formulation comprising a therapeutically effective amount of a compound described herein, or a pharmaceutically acceptable salt thereof, and a pharmaceutically acceptable carrier. In an exemplary embodiment, the invention is a pharmaceutical formulation comprising a therapeutically effective amount of a compound of a formula described herein, or a pharmaceutically acceptable salt thereof, and a pharmaceutically acceptable carrier.

In an exemplary embodiment, the invention is a pharmaceutical formulation described herein, wherein the formulation is in a unit dosage form.

As used herein a "pharmaceutical formulation" refers to a preparation of one or more of the compounds described herein, or physiologically acceptable salts or solvates (including hydrates) thereof, with other chemical components such as physiologically suitable carriers and excipients.

Pharmaceutical formulations containing compounds of Formulas I, and any compound described herein may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, a dose ranges from about 0.1 mg to about 7000 mg, preferably about 1 mg to about 100 mg, and more preferably, about 25 mg to about 50 mg, in single or divided doses. In some embodiments, a dose may range from about 50 mg to about 500 mg, and preferably, about 100 mg to about 500 mg. Such doses may be administered 1, 2, 3, 4, 5, 6 or more times in a day. It may be recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Pharmaceutical formulations for use in accordance with the present invention thus may be formulated in a conventional manner using one or more physiologically acceptable carriers comprising excipients and auxiliaries, which facilitate processing of the active compounds into preparations which, can be used pharmaceutically. The carriers must be acceptable in the sense of being compatible with the other ingredients of the formulation and not deleterious to the recipient thereof. Proper formulation is dependent upon the route of administration chosen.

Compounds that inhibit T-Channels can be formulated as pharmaceutical formulations and administered to a mammalian subject, such as a human patient in a variety of forms adapted to the chosen route of administration, i.e., oral, rectal, nasal (e.g., sprays, nebulizers, etc.), topical (including dermal, buccal, sublingual, and intraocular), or parenteral, by intravenous, intramuscular, topical, transdermal, intradermal, intraarticular, or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar or alginic acid or a salt thereof such as sodium alginate.

In addition, an enteric coating may be useful as it is may be desirable to prevent exposure of the compounds of the invention to the gastric environment.

Pharmaceutical formulations, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia. All formulations for oral administration should be in dosages suitable for the chosen route of administration.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the formulation. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical formulations for parenteral administration include aqueous and non-aqueous sterile injection solutions, which may contain anti-oxidants, buffers, bacteriostats and solutes, which render the formulation isotonic with the blood of the intended recipient. Formulations also include aqueous and non-aqueous sterile suspensions, which may include suspending agents and thickening agents. Pharmaceutical formulations for parenteral administration in an aqueous solution contain the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

The compounds of the present invention may also be formulated in rectal formulations such as suppositories or retention enemas, using, e.g., conventional suppository bases such as cocoa butter, polyethylene glycol, or other glycerides.

Depending on the severity and responsiveness of the condition to be treated, dosing can also be a single administration of a slow release formulations, with course of treatment lasting from several days to several weeks or until cure is effected or diminution of the disease state is achieved. The amount of a formulation to be administered will, of course, be dependent on many factors including the subject being treated, the severity of the affliction, the manner of administration, the judgment of the prescribing physician. The compounds of the invention may be administered orally or via injection at a dose from 0.001 to 250 mg/kg per day. The dose range for adult humans is generally from 0.5 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound described herein and/or from Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

It should be understood that in addition to the ingredients particularly mentioned above, the formulations of this invention may include other agents conventional in the art having regard to the type of formulation in question, for example those suitable for oral administration may include flavoring agents.

The formulations may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Formulations comprising a compound of the present invention formulated in a compatible pharmaceutical carrier may also be placed in an appropriate container and labeled for treatment of an indicated condition.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a compound, formulation or method is disclosed herein as comprising A and B, the alternative embodiment for that compound, formulation or method of "consisting essentially of A and B" and the alternative embodiment for that compound, formulation or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a compound or formulation is described as "consisting essentially of" the listed components, the compound or formulation contains the components expressly listed, and may contain other components which do not substantially affect the condition being treated. That is, the compound or formulation either does not contain any other components which do substantially affect the condition being treated other than those components expressly listed; or, if the compound or formulation does contain extra components other than those listed which substantially affect the condition being treated, the compound or formulation does not contain a sufficient concentration or amount of those extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed.

The following examples are provided to illustrate, but not limit, the invention. The compounds disclosed herein are numbered and proceeded by the prefix EX- or AFA-.

EXAMPLES

Example A

Figure 1B:
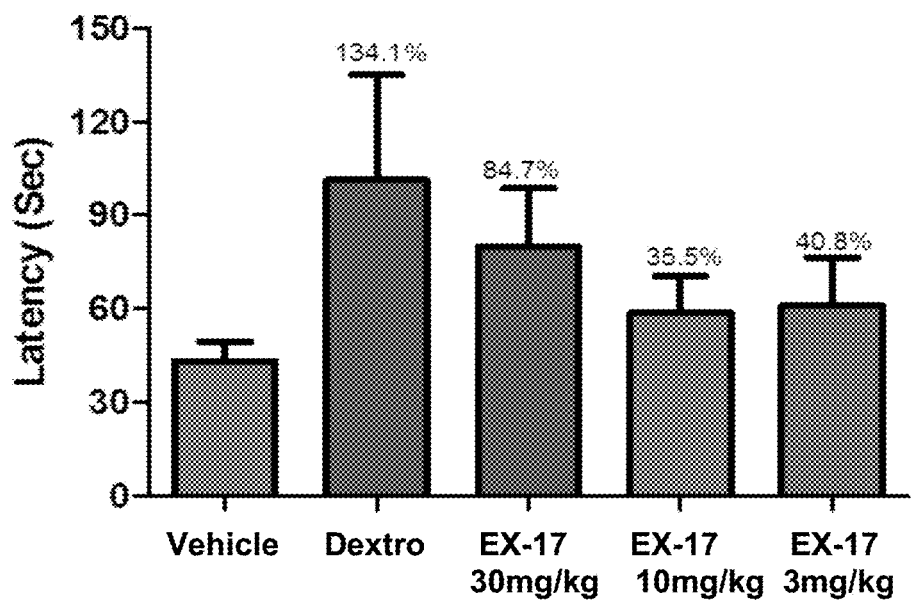
FIG. 1B. Effects of EX-17 at three doses (3, 10 and 30 mg/kg) and dextromethorphan (60 mg/kg) on the latency to first cough event were determined in citric acid-induced cough in guinea pigs. EX-17 (30 mg/kg) and dextromethorphan (60 mg/kg) caused significant increases the latency compared with the vehicle-treated control group using one-way ANOVA followed by Fisher's LSD post-hoc test (to be double checked).

In Vivo Effects of EX/AFA Compounds in a Representative Hypersensitive Cough Model in Guinea Pigs Guinea pigs (male, 280 g body weight, Hartley Crl:HA, Charles River) were maintained in temperature 21±2° C., humidity 55±10%, 12 hours on-12 hours off light cycle, with food and water ad libitum for at least 1 week before testing. Cough was induced with citric acid aerosol inhalation and cough assessment by human manual score (*Gallico*, Borghi et al. 1994). Individual animals were placed in a 4 L plexiglas observation chambers continuously filled with 17.5% citric acid aerosol. Animal cough counts were recorded for 5 min. Coughs can be recognized on the basis of sound associated with a rapid inspiration followed by a rapid expiration. Only the animal with cough counts >=10 times/5 min was selected for experiment. The selected animal was then randomized divided into 5 groups, n=8/group. Five days after screening test, the representative AFA-compound, EX-17 at 0, 3, 10 and 30 mg/kg were administered 30 minutes while the benchmark dextromethorphan hydrobromide (60 mg/kg, p.o.) 60 minutes prior to the citric acid inhalation, based on their PK profiles. EX-17 produced a dose-dependent inhibition of the number of cough events with reduction of 7.2, 23.3 and 36.8% at dose of 3, 10 and 30 mg/kg, respectively (FIG. 1A). At 30 mg/kg EX-17 produced comparable inhibition as dextromethorphan (40.0% at 60 mg/kg, p.o.). The latency to the first cough has been used as an additional parameter to evaluate antitussive property. EX-17 also caused increases in the latencies of the first cough in a dose-dependent manner. Only at 30 mg/kg EX-17 and dextromethorphan hydrobromide (60 mg/kg, p.o.) reached significance under the experimental conditions (FIG. 1B).

Figure 2A:
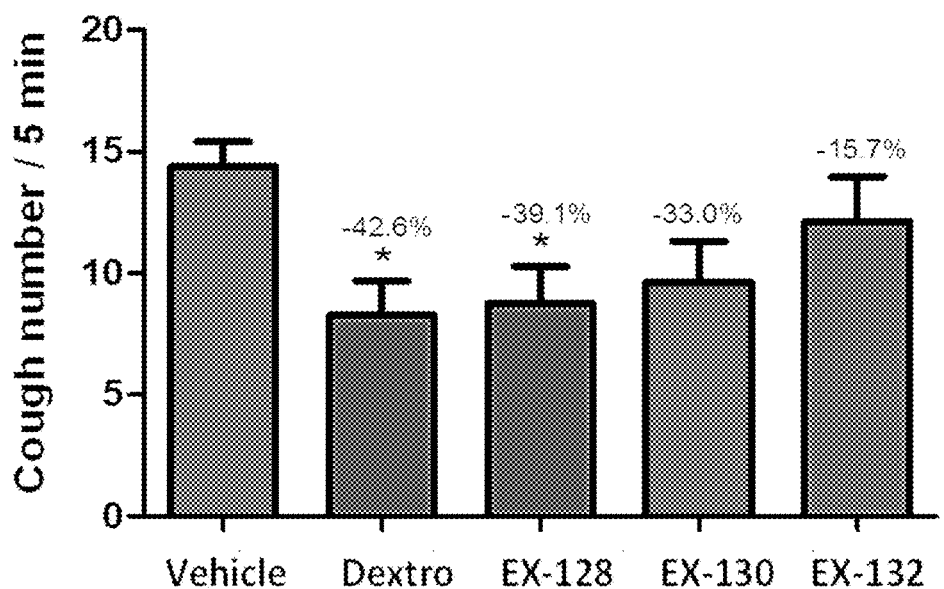
FIG. 2A. Effects of three compounds EX-128 (AFA-279), EX-130 (AFA-281) and EX-132 (AFA-322) (each 30 mg/kg) and the benchmark dextromethorphan (60 mg/kg/kg) on the number of cough events were determined in a model of citric acid-induced cough in naïve, conscious guinea pigs. All test compounds were formulated with 0.5% hydroxyl Propyl Cellulose and given via p.o. Data are given as mean±SEM of n=8 animals per group. P-value (<0.05 indicated by *) represent significant difference compared with the vehicle-treated control group using one-way ANOVA followed by Fisher's LSD post-hoc test.
Figure 2B:
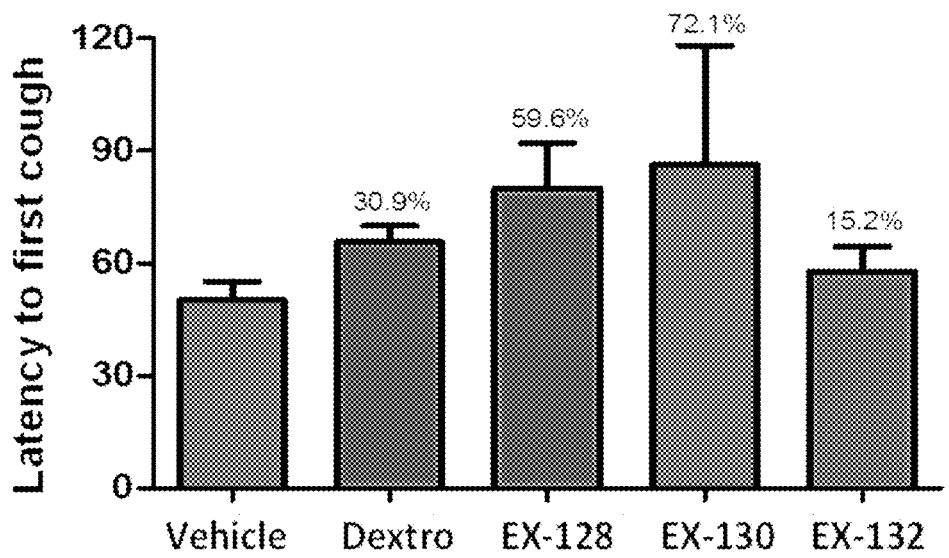
FIG. 2B. Effects of three compounds EX-128, EX-130 and EX-132 and dextromethorphan on the latency to first cough event were determined in citric acid-induced cough in guinea pigs. There is a trend of increasing the latency, but not reaching significant difference compared with the vehicle-treated control group using one-way ANOVA followed by Fisher's LSD post-hoc test.

Using the same test protocol, three more representative EX-compounds EX-128, -130 and -132 (each 30 mg/kg, p.o.) or vehicle were tested by orally administering 30 minutes while dextromethorphan hydrobromide (60 mg/kg, p.o.) 60 minutes prior to the citric acid inhalation, based on their PK profiles. Compared to the vehicle control, compounds EX-128 and dextromethorphan significantly reduced the number of cough events with reduction of 39.1% and 42.6%, respectively (FIG. 2A). EX-130 and -132 showed a trend towards reducing the number of cough events with reduction of 33% and 15.7, respectively, without reaching significance. The latencies to the first cough were increased with three compounds and the benchmark (FIG. 2B).

REFERENCES

Canning, B. J. and Chou, Y. L. (2004). "Cough Sensors. I. Physiological and Pharmacological Properties of the Afferent Nerves Regulating Cough" in "Pharmacology and Therapeutics of Cough" ed. Chung and Widdicomb, pp 23-47, Handbook of Experimental Pharmacology ISSN 0171-2004.

Gallico, L., A. Borghi, C. Dalla Rosa, R. Ceserani and S. Tognella (1994). "Moguisteine: a novel peripheral non-narcotic antitussive drug." Br J Pharmacol 112(3): 795-800.

Irwin, R. S., M. J. Rosen and S. S. Braman (1977). "Cough. A comprehensive review." *Arch Intern Med* 137(9): 1186-1191.

Kase, Y., Y. Wakita, G. Kito, T. Miyata, T. Yuizono and M. Kataoka (1970). "Centrally-induced coughs in the cat." *Life Sci* 9(1): 49-59.

North, R. A. (2016). "P2X receptors." Philos Trans R Soc Lond B Biol Sci 371(1700).

Pachuau, J, Martin-Caraballo, M. (2007). Expression pattern of T-type Ca(2+) channels in embryonic chick nodose ganglion neurons. Dev Neurobiol. 67(14):1901-14.

Example B: In Vivo Effects of AFA/EX Compounds in Two Representative Itching Models in Mice A representative panel of AFA/EX compounds was investigated on a variety of recombinant human ion channels expressed in mammalian cells and on native ion channels in dissociated rat dorsal root ganglion (DRG) neurons. As shown in Table 1, the selected 10 AFA-compounds produced differential modulations on different ion currents mediated by the selected ion channels. Thus, this panel of compounds was next investigated on their effects on itching scratching behavior in two well-established itching models in mice.

Neck model of itch was employed. Mice (C57BL/6, male, 3-4 months old) were shaved at the nape of the neck 2-3 days before experiments. On the day of behavioral testing mice were individually placed in small plastic chambers (12 cm L×9.5 W×12 H) that inserted into an ordinary homecage at least 30 min for habituation and recorded baseline of behavior using a video camera and a piezoelectric floor sensor operated by a validated homecage behavioral monitory system, SmartCage, which can monitor multiple mouse scratching behaviors simultaneously.

Treatment with an individual test article (10 representative AFA-compounds, each at 30 mg/kg) or vehicle (0.5% hydroxyl propyl cellulose aqueous solution containing 2% DMSO) were intraperitoneally (i.p.) injected 30 min prior to itching induction. Mice were given an intradermal injection of 50 μl of a pruritogen, chloroquine or histamine into the nape of the neck. Immediately after the injection, mice were returned to their chambers and were continually recorded by the piezoelectric floor sensor for 30 min. Human manual scoring of itching scratch behavior in real-time and confirmed by video and/or piezoelectric recordings offline. The itch behavior was quantified by counting the number of scratches in a blinded to the treatment manner. A scratch was counted when a mouse lifted its hindpaw to scratch the shaved region and returned the paw to the floor or to the mouth for licking. The piezoelectric signals with a larger and regular waveform distinguished from normal homecage activity were analyzed off-line to objectively quantifying scratch episodes and durations.

Figure 3A:
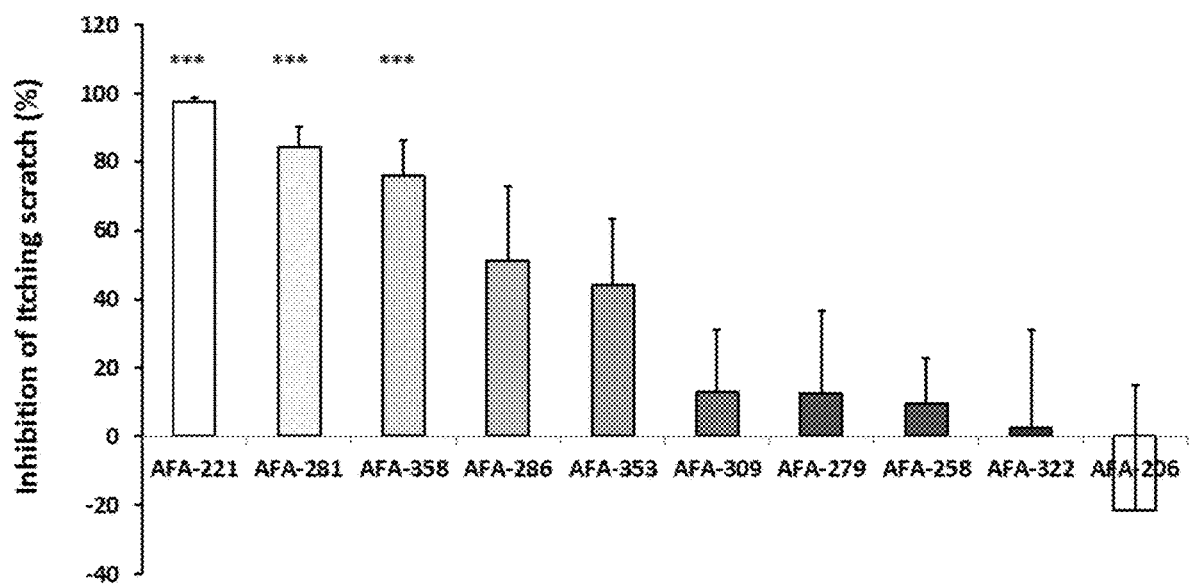
FIG. 3A and FIG. 3B: Effects of AFA compounds on inhibition of itching scratching behavior in two well-established itching models in mice. AFA-221 (EX-31), AFA-281 (EX-130), AFA-358, AFA-286 (EX-146), AFA-353, AFA-309, AFA-279 (EX-128), AFA-258 (Z944 from Zalicus Pharmaceuticals), AFA-322 (EX-132) and AFA-206 (EX-55).
Figure 3B:
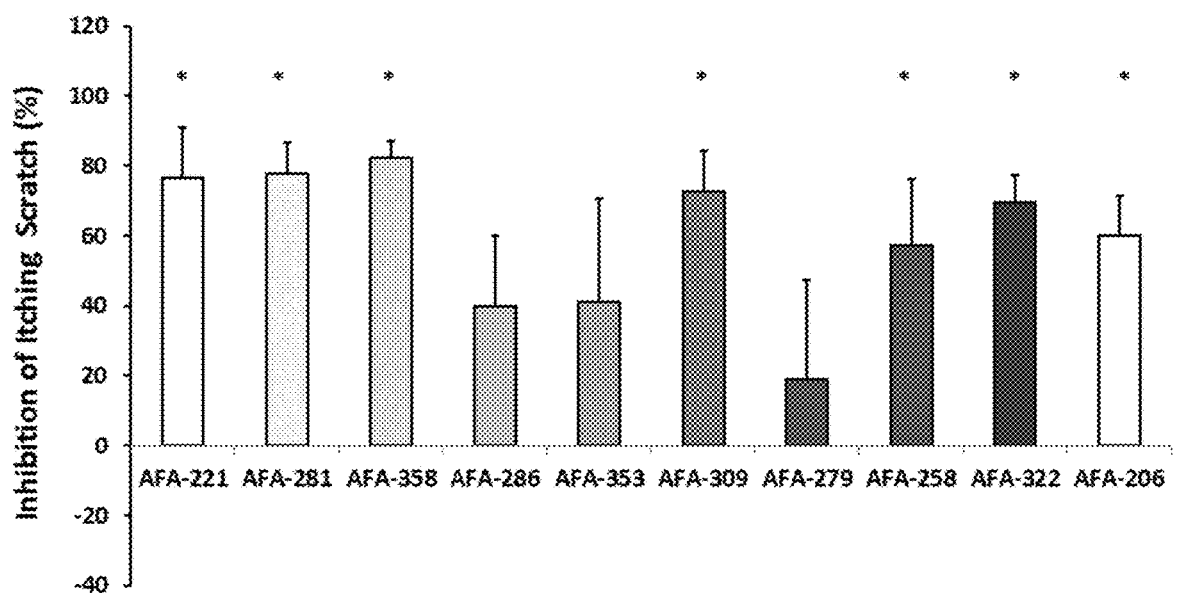

These studies revealed unexpected findings that compounds produced differential modulation of itch scratch behavior in these two different itching models despite those compounds with similar potency against T-type Cav3.2 channels (FIG. 3A), AFA-221 (EX-31), AFA-28 (EX-130) and AFA-358 produced potent and equal efficacy against both chloroquine- and histamine-induced itching. while AFA-309. AFA-258 (Z944), AFA-322 (EX-132) and AFA-206 (EX-55) preferentially inhibited histamine-induced itching (FIG. 3B).

In conclusion, using an itching scratch behavior phenotypic analysis, one can identify novel compounds for potential treatment of chronic itch diseases.

TABLE 1

Effects of representative AFA Compounds on recombinant and native ion channels

| Compound | hCav3.2 Channel | | hCav2.2 | hCav1.2 | hiPSC INa | hNav1.5 | Inhibition of Currents in rat DRG | | | | | hERG |
|---|---|---|---|---|---|---|---|---|---|---|---|---|
| | $IC_{50}$ μM | % Use Dep. | $IC_{50}$ μM | $IC_{50}$ (μM) | $IC_{50}$ μM | $IC_{50}$ μM | T $IC_{50}$ μM | $I_{Na}$ $IC_{50}$ μM | Na/T | $I_K$ $IC_{50}$ μM | K/T | $IC_{50}$ μM |
| AFA-221 | 0.084 | 28.3 | 47% at 3 μM | | | | | 3.6 | 43 | ~30 | 357 | 31% at 1 μM |
| AFA-281* | 0.179 | 13.9 | >30 | | 31.35 | >100 | 0.6 | >100 | >557 | >100 | >557 | 8 |
| AFA-358 | 1.013 | | 0.74 | | | | | >30 | >30 | >30 | >30 | 59% at 1 μM |
| AFA-286* | 0.069 | 20.1 | 2.52 | 4.63 | 27.83 | 9.7 | | 8.7 | 127 | >100 | >1457 | 1.2 |
| AFA-353 | 10.36 | | 8.87 | | | | | >100 | >10 | >100 | >10 | 23% at 1 μM |
| AFA-309* | 0.141 | 4.2 | 15.61 | >30 | 0% at 3 μM | 25.8 | | >30 | >212 | >30 | >212 | >30 |
| AFA-279* | 0.113 | 21.3 | >10 | | 83.45 | 76.4 | 0.19 | >100 | >1115 | >100 | >1115 | 6.7 |
| AFA-258 | 0.195 | 17.6 | >30 | >30 | 21.43 | >100 | 0.2 | >100 | >513 | >100 | >513 | 9.5 |
| AFA-322* | 0.138 | 25.6 | 3.09 | | 51.64 | 23.5 | 0.15 | 14.3 | 103 | >100 | >723 | 9.2 |
| AFA-206 | 0.067 | 8.2 | | | | | | 20.3 | 303 | 6.8 | 102 | 50% at 1 μM | h = human isoform; Use Dep = use dependent inhibition; DRG = dorsal root ganglion; hERG = human ether-a-go-go related gene (hERG) potassium ($K^+$) channels

ADDITIONAL REFERENCES

Avdonin P V, Bailer F R, Tkachuk V A (2000) Ca2+-agonistic effect of a T-type channel Mocker mibefradil (Ro 40-5967). Membr Cell Biol 13:645-655.

Caviedes B E, Herranz J L (2001) [Use of antiepileptic drugs in non epileptic disorders]. Rev Neurol 33:241-249.

Chaplan S R, Bach F W, Pogrel J W, Chung J M, Yaksh T L (1994) Quantitative assessment. of tactile allodynia in the rat paw. Journal of neuroscience methods 53:55-63.

Chaudhry V, Rowinsky E K, Sartorius S E, Donehower R C, Comblath D R (1994) Peripheral neuropathy from taxol and cisplatin combination chemotherapy: clinical and electrophysiological studies. Annals of neurology 35:304-311.

Choi S, Na H S, Kim J, et al. (2007) Attenuated pain responses in mice lacking Ca(V)3.2 T-type channels. Genes Brain Bebav 6:425-431.

Cribbs L L, Gomora J C, Daud A N, Lee J H, Perez-Reyes E (2000) Molecular cloning and functional expression of Ca(v)3.1c, a T-type calcium channel from human brain. FEBS Lett 466:54-58.

Decosterd I, Woolf C J (2000) Spared nerve injury: a animal model of persistent peripheral neuropathic pain. Pain 87:149-158.

Gomora J C, Daud A N, Weiergraber M, Perez-Reyes E (2001) Block of cloned human T-type calcium channels by succinimide antiepileptic drugs. Mol Pharmacol 60:1121-1132, Han H A, Cortez M A, Snead O C III. (2012) $GABA_B$ Receptor and Absence Epilepsy. In: Noebels J L, Avoli M, Rogawski M A, Olsen R W. Delgado-Escueta A V, editors. Jasper's Basic Mechanisms of the Epilepsies [Internet]. 4th edition. Bethesda (Md.): National. Center for Biotechnology Information (US).

Huguenard J R (1996) Low-voltage-activated (T-type) calcium-channel genes identified. Trends Neurosci 21:451-452.

Huguenard J R (2002) Block of T-Type Ca(2+) Channels Is an important Action of Succinimide Antiabsence Drugs. Epilepsy Curr 2:49-52.

Jagodic M M, Pathirathna S, Joksovic P M, Lee W, Nelson M T, Naik A K, Su P, Jevtovic-Todorovic V, Todorovic S M (2008) Upregulation of the T-type calcium current in small rat sensory neurons after chronic constrictive injury of the sciatic nerve. J Neurophysiol 99:3151-3156.

Jagodic M M, Pathirathna S, Nelson M T, Mancuso S, Joksovic P M, Rosenberg E R, Bayliss D A, Jevtovic-Todorovic V, Todorovic S M (2007) Cell-specific alterations of T-type calcium current in painful diabetic neuropathy enhance excitability of sensory neurons. J Neurosci 27:3305-3316.

Jarvis M F, Scott V E, McGaraughty S, Chu K L, Xu J. Niforatos W, Milicic I, Joshi S, Zhang Q, Xia Z (2014) A peripherally acting, selective T-type calcium channel blocker, ABT-639, effectively reduces nociceptive and neuropathic pain in rats. Biochemical pharmacology 89:536-544.

Jenkins I D, Lacrampe F, Ripper J, Alcaraz L, Le P V, Nikolakopoulos G, de Almeida Leone P, White R H, Quinn R J (2009) Synthesis of four novel natural product inspired scaffolds for drug discovery. The Journal of organic chemistry 74:1304-1313.

Kim S H, Chung J M (1992) An experimental model for peripheral neuropathy produced by segmental spinal nerve ligation in the rat Pain, 50(3):355-63.

Kraus R L, Li Y, Gregan Y, Gotter A L, Uebele V N, Fox S V, Doran S M, Barrow J C, Yang Z Q, Reger T S, Koblan K S, Renger J J (2010) in vitro characterization of T-type calcium channel antagonist TTA-A2 and in vivo effects on arousal in mice. J Pharmacol Exp Ther 335:409-417.

Latham J R, Pathirathna S, Jagodic M M, Choe W J, Levin M E, Nelson M T, Lee W Y, Krishnan K, Covey D E, Todorovic S M, Jevtovic-Todorovic V (2009) Selective T-type calcium channel blockade alleviates hyperalgesia in ob/ob mice. Diabetes 58:2656-2665.

Lee M (2014) Z944: a first in class T-type calcium channel modulator for the treatment of pain. Journal of the peripheral nervous system: JPNS 19 Suppl 2:S11-12.

Messinger R B, Naik A K, Jagodic M M, Nelson M T, Lee W Y, Choe W J, Orestes P. Latham J R, Todorovic S M, Jevtovic-Todorovic V (2009) In vivo silencing of the Ca(V)3.2 T-type calcium channels in sensory neurons alleviates hyperalgesia in rats with streptozocin-induced diabetic neuropathy. Pain 145:184-195.

Nahab F B, Handforth A, Brown T, et al., (2012) Octanoic acid suppresses harmaline-induced tremor in mouse model of essential tremor. Neurotherapeutics, 9:635-638

Nelson S C, Friedman H S, Oakes W J, Halperin E C, Tien R, Fuller G N, Hockenberger B, Scroggs M W, Moncino M, Kurtzberg J, et al. (1992) Successful therapy for trilateral retinoblastoma. Am J Ophthalmol 114:23-29.

Perez-Reyes F (2003) Molecular physiology of low-voltage-activated t-type calcium channels. Physiol Rev 83:117-161.

Perez-Reyes E (2010) G protein-mediated inhibition of Cav3.2 T-type channels revisited. Molecular pharmacology 77:136-138.

Perez-Reyes E, Van Deusen A L, Vitko I (2009) Molecular Pharmacology of Human Cav3.2 T-Type Ca2+ Channels: Block by Antihypertensives, Antiarrhythmics, and Their Analogs. Journal of Pharmacology and Experimental Therapeutics 328:624-627.

Pexton T, Moeller-Bertram T, Schilling J M, Wallace M S (2011) Targeting voltage-gated calcium channels for the treatment of neuropathic pain: a review of drug development. Expert opinion on investigational drugs 20:1277-1284.

Pogatzki-Zahn E M, Wagner C, Meinhardt-Renner (2003) Spinal glutamate receptor antagonists differentiate primary and secondary mechanical hyperalgesia caused by incision. Pain 105(1-2):97-107.

Sanguinetti, M C, Jiang C, Curran M E, Keating M T (1995) A mechanistic link between an inherited and an acquired cardiac arrhythmia: hERG encodes the IKr potassium channel. *Cell*, 81:299-307, Talley E M, Cribbs L L, Lee J H, Daud A, Perez-Reyes E, Bayliss D A (1999) Differential distribution of three members of a gene family encoding low voltage-activated (T-type) calcium channels. J Neurosci 19:1895-1911, Todorovic S M, Jevtovic-Todorovic V (2011) T-type voltage-gated calcium channels as targets for the development of novel pain therapies. British journal of pharmacology 163:484-495.

Tringham E, Powell K L, Cain S M, Kuplast K, Mezeyova J, Weerapura M, Eduljee C. Jiang X, Smith P, Morrison J L, Jones N C, Braine E, Rind G, Fee-Maki M, Parker D, Pajouhesh H, Parmar M, O'Brien T J, Snutch T P (2012) T-type calcium channel blockers that attenuate thalamic burst firing and suppress absence seizures. Science translational medicine 4:121ra119.

Uebele V N, Goner A L, Nuss C E, Kraus R L, Doran S M, Garson S L, Reiss D R, Li Y, Barrow J C, Reger T S, Yang Z Q, Ballard J E, Tang C, Metzger J M, Wang S P, Koblan K S, Renger J J (2009) Antagonism of I-type calcium channels inhibits high-fat diet-induced weight gain in mice. J Clin Invest 119:1659-1667.

Wang Y, Liu J J, Dransfield P J, Zhu L, Wang Z, Du X, Jiao X, Su Y, Li A R, Brown S P, Kasparian A. Vimolratana M, Yu M, Pattaropong V, Houze J B, Swaminath G, Tran T, Nguyen K, Guo Q, Zhang J, Zhuang R, Li F, Miao L, Bartberger M D, Correll T L, Chow D, Wong S, Luo J, Lin D C, Medina J C (2013) Discovery and Optimization of Potent GPR40 Full Agonists Containing Tricyclic Spirocycles. ACS medicinal chemistry letters 4:551-555.

Xiang Z, Thompson A D, Brogan J T, Schulte M L, Melancon B J, Mi D, Lewis L M, Zou B, Yang L, Morrison R, Santomango T, Byers F, Brewer K, Aldrich J S, Yu H, Dawson E S, Li M, McManus O, Jones C K, Daniels J S, Hopkins C R, Xie X S, Conn P J, Weaver C D, Lindsley C W (2011) The Discovery and Characterization of ML218: A Novel, Centrally Active I-Type Calcium Channel inhibitor with Robust Effects in STN Neurons and in a Rodent Model of Parkinson's Disease. ACS chemical neuroscience 2:730-742.

Xie X, Brogan J T, Schulte M L, Mi D, Yu H, Dawson E S, Li M, McManus O, Engers J, Lewis L M, Thompson A, Jones C K, Weaver C D, Lindsley C W (2010) Scaffold Hopping Affords a Highly Selective in vitro and in vivo T-Type Calcium Inhibitor Probe Free From IP issues. In: Probe Reports from the NTH Molecular Libraries Program Bethesda (M D).

Xie X, Lancaster B, Peakman T, Garthwaite J (1995) Interaction of the antiepileptic drug lamotrigine with recombinant rat brain type IIA Na+ channels and with native Na+ channels in rat hippocampal neurones. Pflugers Archiv: European journal of physiology 430:437-446.

Xie X, Van Deusen A L, Vitko I, Babu D A, Davies L A, Huynh N, Cheng H, Yang N, Barrett P Q, Perez-Reyes E (2007) Validation of high throughput screening assays against three subtypes of Ca(v)3 T-type channels using molecular and pharmacologic approaches. Assay and drug development technologies 5:191-203.

Yang Z Q, Barrow J C, Shipe W D, Schlegel K A, Shu Y, Yang E V, Lindsley C W, Rittle K E, Bock M G, Hartman G D, Uebele V N, Nuss C E, Fox S V, Kraus R L, Doran S M, Connolly T M, Tang C, Ballard J E, Kuo Y, Adarayan E D, Prueksaritanont T, Zrada M M, Marino M J, Graufelds V K, DiLella A G, Reynolds I J, Vargas H M, Bunting P B, Woltmann R F, Magee M M, Koblan K S, Renger J J (2008) Discovery of 1,4-substituted piperidines as potent and selective inhibitors of I-type calcium channels. J Med Chem 51:6471-6477.

Yue J, Liu L, Liu. Z, Shu B. Zhang Y (2013) Upregulation of T-type Ca2± channels in primary sensory neurons in spinal nerve injury. Spine 38:463-470.

Zhang Y F, Gibbs J W, 3rd, Coulter D A (1996) Anticonvulsant drug effects on spontaneous thalamocortical rhythms in vitro: ethosuximide, trimethadione, and dimethadione. Epilepsy Res 23:15-36.

What is claimed is:

1. A method of treating hypersensitive cough, the method comprising the step of administering a therapeutically effective amount of a compound, or a pharmaceutically acceptable salt thereof, wherein the compound is:

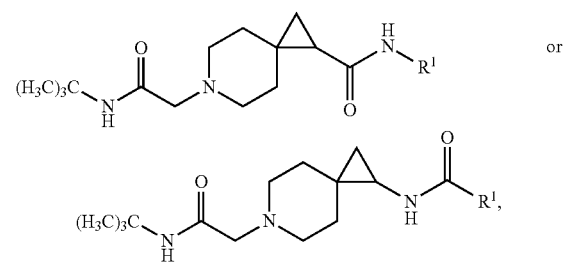

wherein R1 is phenyl substituted with one to three substituents, each of which is a member selected from the group consisting of F, Cl, and CF3, thereby treating hypersensitive cough.

2. The method of claim 1, wherein the compound is:

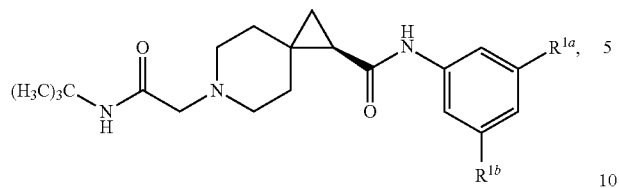

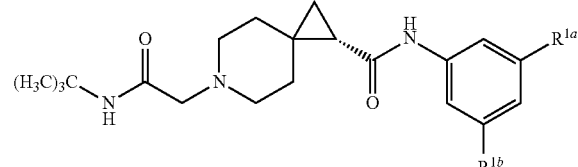

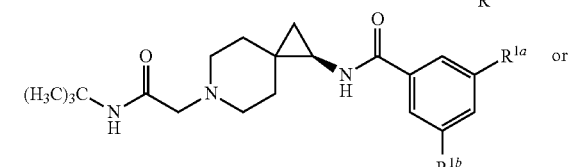

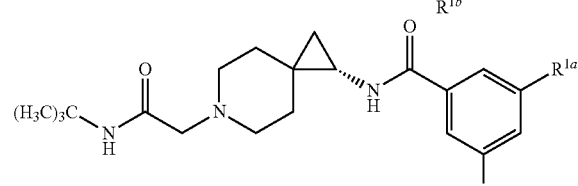

wherein R1a and R1b are members each independently selected from the group consisting of F, Cl, and CF3.

3. The method of claim 1, wherein the compound is:

EX-17
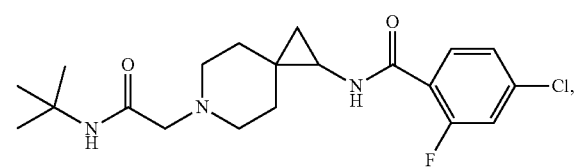

EX-128
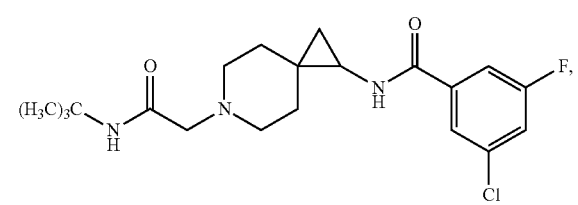

-continued

EX-130
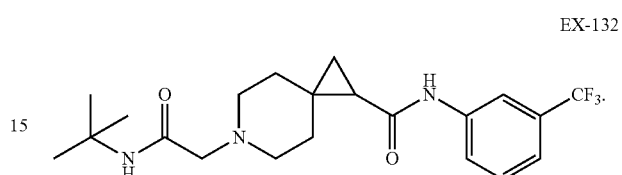

EX-132
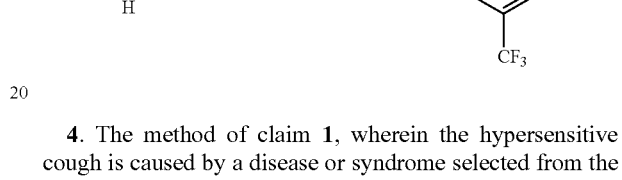

4. The method of claim 1, wherein the hypersensitive cough is caused by a disease or syndrome selected from the group consisting of COPD, asthma, GI reflux, post-nasal drip syndrome and chronic exposure to pollutants.

5. The method of claim 1, wherein the compound is administered orally or nasally.

6. The method of claim 1, wherein the compound is:

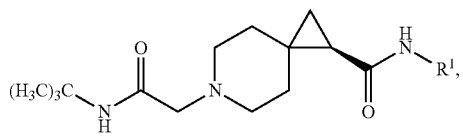

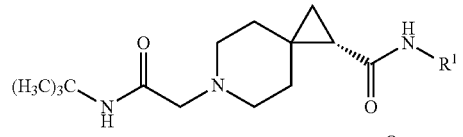

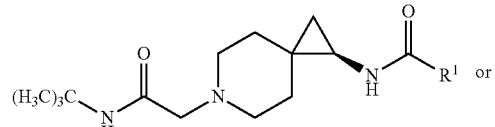

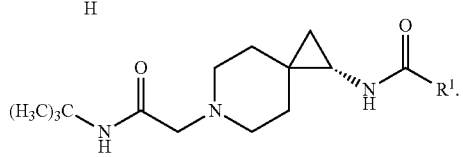

* * * * *